US011123387B2

(12) United States Patent
Newman et al.

(10) Patent No.: US 11,123,387 B2
(45) Date of Patent: Sep. 21, 2021

(54) METHOD AND COMPOSITIONS FOR TREATING VIRAL INFECTION

(71) Applicant: PHOENIX BIOTECHNOLOGY, INC., San Antonio, TX (US)

(72) Inventors: Robert A. Newman, Surry, ME (US); Otis C. Addington, San Antonio, TX (US)

(73) Assignee: PHOENIX BIOTECHNOLOGY, INC., San Antonio, TX (US)

( * ) Notice: Subject to any disclaimer, the term of this patent is extended or adjusted under 35 U.S.C. 154(b) by 0 days.

(21) Appl. No.: 16/803,488

(22) Filed: Feb. 27, 2020

(65) Prior Publication Data
US 2020/0206287 A1    Jul. 2, 2020

Related U.S. Application Data

(63) Continuation of application No. 16/779,840, filed on Feb. 3, 2020, now Pat. No. 10,874,704, which is a continuation of application No. 16/747,637, filed on Jan. 21, 2020, which is a continuation of application No. 16/424,902, filed on May 29, 2019, now Pat. No. 10,702,567, which is a continuation-in-part of application No. 16/276,063, filed on Feb. 14, 2019, now Pat. No. 10,596,186, which is a continuation of application No. PCT/US2018/042226, filed on Jul. 16, 2018, which is a continuation-in-part of application No. PCT/US2017/051553, filed on Sep. 14, 2017, said application No. 16/276,063 is a continuation-in-part of application No. PCT/US2017/051553, filed on Sep. 14, 2017.

(60) Provisional application No. 62/698,365, filed on Jul. 16, 2018, provisional application No. 62/394,504, filed on Sep. 14, 2016, provisional application No. 62/853,838, filed on May 29, 2019.

(51) Int. Cl.
*A61K 36/24* (2006.01)
*A61K 31/56* (2006.01)
*A61P 31/14* (2006.01)
*A61K 31/7048* (2006.01)

(52) U.S. Cl.
CPC .............. *A61K 36/24* (2013.01); *A61K 31/56* (2013.01); *A61K 31/7048* (2013.01); *A61P 31/14* (2018.01); *A61K 2236/37* (2013.01); *A61K 2236/39* (2013.01)

(58) Field of Classification Search
CPC .... A61K 31/7048; A61K 31/56; A61K 36/24; A61P 31/14
See application file for complete search history.

(56) References Cited

U.S. PATENT DOCUMENTS

| | | |
|---|---|---|
| 5,135,745 A | 8/1992 | Ozel |
| 5,869,060 A | 2/1999 | Soon |
| 5,977,174 A | 11/1999 | Bradley |
| 6,217,874 B1 | 4/2001 | Johannsen |
| 6,565,897 B2 | 5/2003 | Selvaraj |
| 7,402,325 B2 | 7/2008 | Addington |
| 8,187,644 B2 | 5/2012 | Addington |
| 8,367,363 B2 | 2/2013 | Addington |
| 8,394,434 B2 | 3/2013 | Addington |
| 8,481,086 B2 | 7/2013 | Addington |
| 9,011,937 B2 | 4/2015 | Addington |
| 9,220,778 B2 | 12/2015 | Addington |
| 9,303,058 B2 | 4/2016 | Leunis |
| 9,358,293 B2 | 6/2016 | Addington |
| 9,877,979 B2 | 1/2018 | Addington |
| 10,226,497 B2 | 3/2019 | Addington |
| 10,729,735 B1 | 8/2020 | Newman et al. |
| 2004/0082521 A1 | 4/2004 | Singh |
| 2004/0247660 A1 | 12/2004 | Singh |
| 2005/0026849 A1 | 2/2005 | Singh |
| 2006/0135443 A1 | 6/2006 | Khodadoust |
| 2006/0234955 A1 | 10/2006 | Pollard |
| 2007/0154573 A1 | 7/2007 | Rashan |
| 2007/0249711 A1 | 10/2007 | Choi |
| 2008/0200401 A1 | 8/2008 | Addington |
| 2011/0105423 A1* | 5/2011 | Shaw ............... A61P 31/16 514/34 |
| 2012/0165279 A1 | 6/2012 | Lee |
| 2013/0267475 A1 | 10/2013 | Addington |

(Continued)

FOREIGN PATENT DOCUMENTS

| | | |
|---|---|---|
| CN | 1301774 A1 | 2/2016 |
| CN | 106562982 A * | 4/2017 |

(Continued)

OTHER PUBLICATIONS

FDA Lanoxin (digoxin) Prescribing Information at https://www.accessdata.fda.gov/drugsatfdadocs/label/2016/020405s013lbl.pdf (2016) (Year: 2016) (retrieved from the internet Nov. 11, 2020).*

(Continued)

*Primary Examiner* — Dennis Heyer
(74) *Attorney, Agent, or Firm* — Innovar, L.L.C.; Rick Matos

(57) ABSTRACT

A method of treating viral infection, such as viral infection caused by a virus of the Filoviridae family, Flaviviridae family (*Flavivirus* genus), *Deltaretrovirus* genus, or Togaviriade family is provided. A composition having at least one cardiac glycoside is used to treat viral infection. The composition can further include at least one triterpene. Alternatively, the composition comprises at least one, at least two, or at least three triterpenes.

11 Claims, 15 Drawing Sheets

(56) References Cited

U.S. PATENT DOCUMENTS

| | | |
|---|---|---|
| 2015/0283191 A1 | 10/2015 | Addington |
| 2016/0000754 A1 | 1/2016 | Stamets |
| 2016/0243143 A1 | 8/2016 | Addington |
| 2016/0354396 A1 | 12/2016 | Mahoney et al. |
| 2017/0130233 A1 | 5/2017 | Lang et al. |
| 2017/0274031 A1 | 9/2017 | Addington |
| 2018/0000852 A1 | 1/2018 | Addington |
| 2018/0042976 A1 | 2/2018 | Addington |
| 2019/0216835 A1 | 7/2019 | Brass |
| 2020/0206288 A1 | 7/2020 | Newman et al. |
| 2020/0222483 A1 | 7/2020 | Newman et al. |

FOREIGN PATENT DOCUMENTS

| | | |
|---|---|---|
| EP | 2260851 A1 | 12/2010 |
| WO | 9932097 A2 | 7/1999 |
| WO | 0064921 A2 | 11/2000 |
| WO | 03099011 A1 | 12/2003 |
| WO | 2013048355 A2 | 4/2013 |
| WO | 2016015634 A1 | 8/2016 |
| WO | 2019055245 A1 | 3/2019 |

OTHER PUBLICATIONS

Grahame-Smith et al. in Brit. Med. J. (1969), 1,286-289 (Year: 1969).*

Yim et al. ("Antiproliferative and antiviral mechanism of ursolic acid and dexamethasone in cervical carcinoma cell lines" in Int. J. Gynecol. Cancer (2006), 16, 2023-2031; abstract).

Newman et al. ("Innovations in clinical & applied evidence-based herbal medicinals" in J. Herbal Pharmacotherapy, (2001) vol. 1, pp. 1-16).

Erdemoglu et al, ("Anti-inflammatory and antinociceptive activity assessment of plants used as remedy in Turkish fold medicine" in J. Ethnopharmacol. Nov. 2003. 89(1), 123-129; abstract).

Adome et al. ("The cardiotonic effect of the crude ethanolic extract of Nerium Oleander in the isolated guinea pig hearts" in Afr. Health Sci. Aug. 2003. 3(2), 77-86).

El-Shazly et al. ("Toxic effect of ethanolic extract of Nerium oleander (apocynaceae) leaves against different developmental stages of Muscina stabulans" in J. Egypt Soc. Parasitol. Aug. 1996, 26(2), 461-473; abstract).

Begum et al. ("Bioactive cardenolides from the leaves of Nerium Oleander" in Phytochemistry Feb. 1999. 50(3), 435-438; abstract).

Zia et al. ("Studies on the constituents of the leaves of Nerium oleander on behavior pattern in mice" in J. Ethnolpharmacol. Nov. 1995. 49(1), 33-39; abstract).

Amarelle et al. ("The antiviral effects f Na,K-ATPas Inhibition: A Minireview" in Int. J. Molec. Sci. (2018), 19, 2154; doi: 10.3990/ijms19072154).

Fumiko et al. ("Ursolic acid as a trypanocidal constituent in rosemary" in Biol. Pharm. Bull. (2002), 25(11), 1485-1487).

Jager et al. ("Pentacyclic triterpene distribution in various plants-rich sources for a new group of multi-potent plant extracts" in Molecules (2009), 14, 2016-2031).

Mishra et al. ("Isolation, characterization and anticancer potential of cytotoxic triterpenes from Betula utilis bark" in PLoS One (2016) 25;11(7):e0159430. Epub Jul. 25, 2016).

Wang et al. ("Improved production and antitumor propertes of triterpene acids from submerged culture of Ganoderma lingzhi" in Molecules (2016), 21, 1395).

L. e Silva et al. ("Bioactive oleanane, lupane and ursane triterpene acid derivatives" in Molecules (2012), 17(10), 12197-12205).

Rui et al. ("Supercritical fluid extraction of eucalyptus globulus bark—a promising approach for triterpenoid production" in Int. J. Mol. Sci. (2012), 13, 7648-7662).

Ayatollahi et al. ("Pentacyclic triterpenes in Euphorbia microsciadia with their T-cell proliferation activity" in Iran. J. Pharm. Res. (2011), 10(2), 287-294).

Wu et al. ("Triterpenoid contents and anti-inflammatory properties of the methanol extracts of ligustrum species leaves" in Molecules (2011), 16(1), 1-15).

Lee et al. ("Effects of hydroxy pentacyclic triterpene acids from forsythia viridissima on asthmatic responses to ovalbumin challenge in conscious guinea pigs" in Biol. Pharm. Bul. (2010), 33(2), 230-237).

Van Kanegan et al. ("Dual activities of the anti-cancer drug candidate PBI-05204 provide neuroprotection in brain slice models for neurodegenerative diseases and stroke" in Nature Scientific Reports (May 2016), 6:25626. doi: 10.1038/srep25626).

Barrows et al. ("A screen of FDA-approved drugs for inhibitors of Zikavirus infection" in Cell Host Microbe (2016), 20, 259-270).

Cheung et al. ("Antiviral activity of lanatoside C against dengue virus infection" in Antiviral Res. (2014) 111, 93-99).

Chung et al. ("Inhibitory effect of ursolic acid purified from *Origanum majoma* L on the acetylcholinesterase" in Mol. Cells (2001), 11(2), 137-143).

Heo et al. ("Ursolic acid of *Origanum majorana* L. reduces Abeta-induced oxidative injury" in Mol. Cells (2002), 13(1), 5-11).

Yoo et al. ("Terpenoids as potential anti-Alzheimer's disease therapeutics" in Molecules (2012), 17(3), 3524-3538) (abstract).

Qian et al. ("Maslinic acid, a natural triterpenoid compound from Olea europaea, protects cortical neurons against oxygen-glucose deprivation-induced injury" in Eur. J. Pharmacol. (2011), 670(1), 148-153; abstract).

Zhang et al. ("Ursolic acid reduces oxidative stress to alleviate early brain injury following experimental subarachnoid hemorrhage"; Neuroscience Letters (2014), 579, 12-17; abstract).

Garcia-Morales et al. ("Anti-inflammatory, antioxidant and anti-acetylcholinesterase activities of Bouvardia temifolia: potential implications in Alzheimer's disease"; Arch. Pharm. Res. (2015), 38(7), 1369-1379).

Li et al. ("Ursolic acid promotes the neuroprotection by activating Nrf2 pathway after cerebral ischemia in mice"; Brain Res. (2013), 1497, 32-39) (abstract).

So et al. ("Anti-ischemic activities of aralia cordata and its active component, oleanolic acid"; Arch. Pharm. Res. (2009), 32(6), 923-932) (abstract).

Rong et al. ("Protective effects of oleanolic acid on cerebral ischemic damage in vivo and H(2)O(2)-induced injury in vitro"; Pharm. Bio. (2011), 49(1), 78-85) (abstract).

Lo et al. ("Dual activities of the anti-cancer drug candidate PBI-05204 provide neuroprotection in brain slice models for neurodegenerative diseases and stroke", Scientific Reports (2016), 6, 25626; doi:10.1038/srep25626).

Karawya et al. ("Phytochemical study of Nerium oleander growing in Egypt. Preliminary investigation", United Arab Republic J. Pharm. Sci. (1970), 11(2), 193-209).

Jaeger et al. ("Pentacyclic triterpene distribution in various plants-rich sources for a new group of multi-potent plant extracts", Molecules (2009), 14(6), 2016-2031).

Siddiqui et al. ("Oleanderol, a new pentacyclic triterpene from the leaves of Nerium oleander", J. Natur. Prod. (1988), 51(2), 229-233).

Yu et al. ("New Polysaccharide from Nerium indicum protects neurons via stress kinase signaling pathway") Brain Research, (2007), 1153, pp. 221-230.

Yogeeswari et al. ("Betulinic Acid and its derivatives: a review of their biological properties" in Curr. Med. Chem. (2005), 12, 657-666).

Wang et al. ("LC/MS/MS Analyses of an Oleander Extract for Cancer Treatment" in Anal. Chem. (2000), 72, 3547-3552).

Bai et al. ("Studies on Chemical Constituents of Japanese Nerium indicum Mill and Their Cytotoxicity in vitro" in J. Anhui Agri. Sci. (2009), 37(20), 9480-9488).

Chudzik et al. ("Triterpenes as Potentially Cytotoxic Compounds" in Molecules (2015) 20, 1610-1625).

Chiang et al. ("Antiviral Activities of Extracts and Selected Pure Constituents of Ocimum Basilicum" in Clin. Exp. Pharm. Phys. (2005), 32, 811-816).

Cichewicz et al. ("Chemistry, Biological Activity and Chemotherapeutic Potential of Betulinic Acid for the Prevention and Treatment of Cancer and HIV Infection" in Medic. Res. Rev. (2004), 24(1), 90-114).

(56) References Cited

OTHER PUBLICATIONS

Dey et al. ("Pharmacological Aspects of Nerium Indicum Mill: A Comprehensive Review" in Pharmacogn. Rev. (2014), 8(16), 156-162).
Cai et al. ("Digitoxin analogues with improved anticytomegalovirus activity" in ACS Med. Chem. Lett. (2014), 5, 395-399).
Boldescu et al. ("Broad-spectrum agents for flaviviral infections: dengue, Zika, and beyond" in Nature Rev. (2017), 16, 565-586).
Grosso et al. ("Suppression of adenovirus replication by cardiotonic steroids" in J. Virol. (2017), 91(3), e01623-16).
Heidary Navid et al. ("Pentacyclic triterpenes in birch bark extract inhibit early step of herpes simplex virus type 1 replication" in Phytomed. (2014), 21, 1273-1280).
Jesus et al. ("Antimicrobial activity of oleanolic and ursolic acids: an update" in Evidence-based Complem. Alt. Med. (2015), ID 620472, 1-14).
Kapoor et al. ("Human Cytomegalovirus Inhibition by Cardiac Glycosides: Evidence for Involvement of the hERG Gene" in Antimicrob. Agents Chemother. (2012), 56(9), 4891-4899).
Kong et al. ("Oleanolic acid and ursolic acid: novel hepatitis C virus antivirals that inhibit NS5B activity" in Antivir. Res (2013), 98, 44-53).
Parikh et al. ("Oleanane triterpenoids in the prevention and therapy of breast cancer: current evidence and future perspectives" in Phytochem. Rev. (Feb. 5, 2014), DOI 10.1007/s11101-014-9337-5; online publication).
Pavlova et al. ("Antiviral activity of betulin, betulin, and betulonic acids against some enveloped and non-enveloped viruses" in Fitoterap. (2003), 74, 489-492).
Amarelle et al. ("Cardiac glycosides decrease influenza virus replication by inhibiting cell protein . . . " in Am. J. Physiol. Lung Cell Mol. Physiol. (2019)m 316: L1094-1106).
Laird et al. ("A novel cell-based high-throughput screen for inhibitors of HIV-1 gene expression and . . . " in J. Antimicrob. Chemotherap. (2014), 69, 988-994).
Ashbrook et al. ("Antagonism of the sodium-potassium ATPase Impairs Chikungunya Virus Infection" in MBio (2016), 7(3), e00693-16).
Dowall et al. ("Antiviral screening of multiple compounds against Ebola virus" in Viruses (2016), 8, 277; doi:10.3390/v8110277).
Guo et al. ("Screening of Natural extracts for inhibitors against Japanese Encephalitis Virus infection" in Antimicrob. Agents Chemother. (2019) doi:10.1128/AAC.02373-19).
Du et al. ("Combinatorial screening of a panel of FDA-approved drugs identifies several . . . " in Biochem. Biophys. Res. Commun. (2019) doi.org/10.1016/j.bbrc2019.11.065).
Kwofie et al. ("Pharmacoinformatics-based indentification of potential bioactive compounds . . . " in Comp. Biol. Med. (2019), 113, 103414).
Ramirez-Ortega et al. ("Proliferation and apoptosis of HELA cells induced by in vitro stimulation with digitalis" in Eur. J. Pharmacol. (2006), 534, 71-76).
Platz et al. ("A novel two-stage interdisciplinary study identifies digoxin as a possible drug for prostate cancer treatment" in Cancer Disc. (2011), 1(1), 69-77; DOI: 10.1158/2159-8274.CD-10-0020).
Lin et al. ("A pilot phase II study of digoxin in patients with recurrent prostate cancer as evident by a rising PSA" in Am. J. Cancer Ther. Pharmacol. (2014), 2(1), 21-32).
Boursi et al. ("Digoxin use and the risk for colorectal cancer" in Pharmacoepidemiol. Drug. Saf. (2014), 23(11), 1147-1153).
Grahame-Smith et al. ("Measurement of digoxin in plasma and its use in diagnosis of digoxin intoxication" in Brit. Med. J. (1969), 1, 286-289)

* cited by examiner

FIG. 1

EBOV

FIG. 2

Inhibition of EBOV after passaging

FIG. 3

MARV

% control infection vs Oleandrin (uM)
- oleandrin
- anvirzel
- PBI 05204

FIG. 4

Inhibition of MARV after passaging

% inhibition vs Oleandrin (uM)
- oleandrin
- PBI 05204
- anvirzel

Vehicle

Extract [10 ug/ml]

Oleandrin [10 ug/ml]

Extract [50 ug/ml]

Oleandrin [50 ug/ml]

Cyclophosphamide huPBMCs + SLB1/pLenti-GFP (HTLV-1+)

Vehicle control

Extract

Oleandrin

METHOD AND COMPOSITIONS FOR TREATING VIRAL INFECTION

CROSS-REFERENCE TO EARLIER FILED APPLICATIONS

The present application claims the benefit of and is a continuation of Ser. No. 16/779,840 filed Feb. 3, 2020, which is a continuation of Ser. No. 16/747,637 filed Jan. 21, 2020, which is a continuation of application Ser. No. 16/424,902 filed May 29, 2019, which is a continuation-in-part of application Ser. No. 16/276,063 filed Feb. 14, 2019, which is a continuation of application No. PCT/US18/42226 filed Jul. 16, 2018, which is a continuation-in-part of application No. PCT/US17/51553 filed Sep. 14, 2017, and said application No. No. PCT/US18/42226 also claims the benefit of provisional application No. 62/698,365 filed Jul. 16, 2018, and said application Ser. No. 16/276,063 is also a continuation-in-part of said application No. PCT/US17/51553, which claims the benefit of provisional application No. 62/394,504 filed Sep. 14, 2016, and said application Ser. No. 16/424,902 claims the benefit of provisional application No. 62/853,838 filed May 29, 2019, the entire disclosures of which are hereby incorporated by reference.

FIELD OF THE INVENTION

The present invention concerns an antiviral composition and its use for treating Flaviviridae infection, Togaviridae infection, or Filoviridae infection in mammals. Some embodiments concern treatment of hemorrhagic viral infection.

BACKGROUND OF THE INVENTION

*Nerium oleander*, a member of the *Nerium* species, is an ornamental plant widely distributed in subtropical Asia, the southwestern United States, and the Mediterranean. Its medical and toxicological properties have long been recognized. It has been proposed for use, for example, in the treatment of hemorrhoids, ulcers, leprosy, snake bites, cancers, tumors, neurological disorders, cell-proliferative diseases.

Extraction of components from plants of *Nerium* species has traditionally been carried out using boiling water, cold water, or organic solvent.

ANVIRZEL™ (U.S. Pat. No. 5,135,745 to Ozel), which is commercially available, contains the concentrated form or powdered form of the hot-water extract of *Nerium oleander*. Muller et al. (*Pharmazie*. (1991) September 46(9), 657-663) disclose the results regarding the analysis of a water extract of *Nerium oleander*. They report that the polysaccharide present is primarily galacturonic acid. Other saccharides include rhamnose, arabinose and galactose. Polysaccharide content and individual sugar composition of polysaccharides within the hot water extract of *Nerium oleander* have also been reported by Newman et al. (*J. Herbal Pharmacotherapy*, (2001) vol 1, pp. 1-16). U.S. Pat. No. 5,869,060 to Selvaraj et al. pertains to extracts of *Nerium* species and methods of production. To prepare the extract, plant material is placed in water and boiled. The crude extract is then separated from the plant matter and sterilized by filtration. The resultant extract can then be lyophilized to produce a powder. U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile extract.

Erdemoglu et al. (*J. Ethnopharmacol.* (2003) November 89(1), 123-129) discloses results for the comparison of aqueous and ethanolic extracts of plants, including *Nerium oleander*, based upon their anti-nociceptive and anti-inflammatory activities.

Organic solvent extracts of *Nerium oleander* are also disclosed by Adome et al. (*Afr. Health Sci.* (2003) August 3(2), 77-86; ethanolic extract), el-Shazly et al. (*J. Egypt Soc. Parasitol.* (1996), August 26(2), 461-473; ethanolic extract), Begum et al. (*Phytochemistry* (1999) February 50(3), 435-438; methanolic extract), Zia et al. (*J. Ethnolpharmacol.* (1995) November 49(1), 33-39; methanolic extract), and Vlasenko et al. (*Farmatsiia*. (1972) September-October 21(5), 46-47; alcoholic extract).

A supercritical fluid extract of *Nerium* species is known (U.S. Pat. Nos. 8,394,434, 8,187,644, 7,402,325) and has demonstrated efficacy in treating neurological disorders (U.S. Pat. Nos. 8,481,086, 9,220,778, 9,358,293, US 20160243143A1) and cell-proliferative disorders (U.S. Pat. No. 8,367,363).

Triterpenes are known to possess a wide variety of therapeutic activities. Some of the known triterpenes include oleanolic acid, ursolic acid, betulinic acid, bardoxolone, maslinic acid, and others. The therapeutic activity of the triterpenes has primarily been evaluated individually rather than as combinations of triterpenes.

Oleanolic acid is in a class of triterpenoids typified by compounds such as bardoxolone which have been shown to be potent activators of the innate cellular phase 2 detoxifying pathway, in which activation of the transcription factor Nrf2 leads to transcriptional increases in programs of downstream antioxidant genes containing the antioxidant transcriptional response element (ARE). Bardoxolone itself has been extensively investigated in clinical trials in inflammatory conditions; however, a Phase 3 clinical trial in chronic kidney disease was terminated due to adverse events that may have been related to known cellular toxicities of certain triterpenoids including bardoxolone at elevated concentrations.

Compositions containing triterpenes in combination with other therapeutic components are found as plant extracts. Fumiko et al. (Biol. Pharm. Bull (2002), 25(11), 1485-1487) discloses the evaluation of a methanolic extract of *Rosmarimus officinalis* L. for treating trypanosomiasis. Addington et al. (U.S. Pat. Nos. 8,481,086, 9,220,778, 9,358,293, US 20160243143 A1) disclose a supercritical fluid extract (SCF; PBI-05204) of *Nerium oleander* containing oleandrin and triterpenes for the treatment of neurological conditions. Addington et al. (U.S. Pat. No. 9,011,937, US 20150283191 A1) disclose a triterpene-containing fraction (PBI-04711) of the SCF extract of *Nerium oleander* containing oleandrin and triterpenes for the treatment of neurological conditions. Jäger et al. (Molecules (2009), 14, 2016-2031) disclose various plant extracts containing mixtures of oleanolic acid, ursolic acid, betulinic acid and other components. Mishra et al. (PLoS One 2016 25; 11(7):e0159430. Epub 2016 Jul. 25) disclose an extract of *Betula utilis* bark containing a mixture of oleanolic acid, ursolic acid, betulinic acid and other components. Wang et al. (Molecules (2016), 21, 139) disclose an extract of *Alstonia scholaris* containing a mixture of oleanolic acid, ursolic acid, betulinic acid and other components. L. e Silva et al. (Molecules (2012), 17, 12197) disclose an extract of *Eriope blanchetti* containing a mixture of oleanolic acid, ursolic acid, betulinic acid and other components. Rui et al. (Int. J. Mol. Sci. (2012), 13, 7648-7662) disclose an extract of *Eucaplyptus globulus* containing a mixture of oleanolic acid, ursolic acid, betulinic acid and other components. Ayatollahi et al. (Iran. J. Pharm. Res. (2011), 10(2), 287-294) disclose an extract of *Euphorbia microsciadia* containing a mixture of oleanolic acid, ursolic acid, betulinic acid and other components. Wu et al. (Molecules (2011), 16, 1-15) disclose an extract of *Ligustrum* species containing a mixture of oleanolic acid, ursolic acid, betulinic acid and other components. Lee et al. (Biol. Pharm. Bull (2010), 33(2), 330) disclose an extract of *Forsythia viridissima* containing a mixture of oleanolic acid, ursolic acid, betulinic acid and other components.

Oleanolic acid (O or OA), ursolic acid (U or UA) and betulinic acid (B or BA) are the three major triterpene components found in PBI-05204 (PBI-23; a supercritical fluid extract of *Nerium oleander*) and PBI-04711 (a triterpene-containing fraction 0-4 of PBI-05204). We (two of the instant inventors) previously reported (Van Kanegan et al., in Nature Scientific Reports (May 2016), 6:25626. doi: 10.1038/srep25626) on the contribution of the triterpenes toward efficacy by comparing their neuroprotective activity in a brain slice oxygen glucose deprivation (OGD) model assay at similar concentrations. We found that PBI-05204 (PBI) and PBI-04711 (Fraction 0-4) provide neuroprotective activity.

Extracts of *Nerium* species are known to contain many different classes of compounds: cardiac glycosides, glycones, steroids, triterpenes, polysaccharides and others. Specific compounds include oleandrin; neritaloside; odoroside; oleanolic acid; ursolic acid; betulinic acid; oleandrigenin; oleaside A; betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21-en-38-oic acid; 3β,27-dihydroxy-12-ursen-38-oic acid; 3β,13β-dihydroxyurs-11-en-28-oic acid; 3β,12α-dihydroxyoleanan-28,13β-olide; 3β,27-dihydroxy-12-oleanan-28-oic acid; and other components.

Viral hemorrhagic fever (VHF) can be caused by five distinct virus families: Arenaviridae, Bunyaviridae, Filoviridae, Flaviviridae, and Paramyxoviridae. The Filoviruses, e.g. Ebolavirus (EBOV) and Marburgvirus (MARV), are among the most pathogenic viruses known to man and the causative agents of viral hemorrhagic fever outbreaks with fatality rates of up to 90%. Each virion contains one molecule of single-stranded, negative-sense RNA. Beyond supportive care or symptomatic treatment, there are no commercial therapeutically effective drugs and no prophylactic drugs available to treat EBOV (Eboval virus) and MARV (Marburg virus) infections, i.e. filovirus infections. Five species of Ebolavirus have been identified: Taï Forest (formerly Ivory Coast), Sudan, Zaire, Reston and Bundibugyo.

The Flaviviruses are positive, single-stranded, enveloped RNA viruses. They are found in arthropods, primarily ticks and mosquitoes, and cause widespread morbidity and mortality throughout the world. Some of the mosquito-transmitted viruses include Yellow Fever, Dengue Fever, Japanese Enchephalitis, West Nile Viruses, and Zikavirus. Some of the tick-transmitted viral infections include Tick-borne Encephalitis, Kyasanur Forest Disease, Alkhurma Disease, Omsk Hemorrhagic Fever. Although not a hemorrhagic infection, Powassan virus is a *Flavivirus*.

Oleandrin, and an extract of *Nerium oleander* have been shown to prevent the incorporation of the gp120 envelope glycoprotein of HIV-1 into mature virus particles and inhibit viral infectivity in vitro (Singh et al., "*Nerium oleander* derived cardiac glycoside oleandrin is a novel inhibitor of HIV infectivity" in Fitoterapia (2013) 84, 32-39).

Oleandrin has demonstrated anti-HIV activity but has not been evaluated against many viruses. The triterpenes oleanolic acid, betulinic acid and ursolic acid have been reported to exhibit differing levels of antiviral activity but have not been evaluated against many viruses. Betulinic acid has demonstrated some anti-viral activity against HSV-1 strain 1C, influenza A H7N1, ECHO 6, and HIV-1. Oleanolic acid has demonstrated some anti-viral activity against HIV-1, HEP C, and HCV H strain NS5B. Ursolic acid has demonstrated some anti-viral activity against HIV-1, HEP C, HCV H strain NS5B, HSV-1, HSV-2, ADV-3, ADV-8, ADV-11, HEP B, ENTV CVB1 and ENTV EV71. The antiviral activity of oleandrin, oleanolic acid, ursolic acid and betulinic acid is unpredictable as far as efficacy against specific viruses. Viruses exist against which oleandrin, oleanolic acid, ursolic acid and/or betulinic acid have little to no antiviral activity, meaning one cannot predic a priori whether oleandrin, oleanolic acid, ursolic acid and/or betulinic acid will exhibit antiviral activity against particular genuses of viruses.

Barrows et al. ("A screen of FDA-approved drugs for inhibitors of Zikavirus infection" in *Cell Host Microbe* (2016), 20, 259-270) report that digoxin demonstrates antiviral activity against Zikavirus but the doses are too high and likely toxic. Cheung et al. ("Antiviral activity of lanatoside C against dengue virus infection" in *Antiviral Res.* (2014) 111, 93-99) report that lanatoside C demonstrates antiviral activity against Dengue virus.

Human T-lymphotropic virus type 1 (HTLV-1) is a retrovirus belonging to the family Retroviridae and the genus deltaretrovirus. It has a positive-sense RNA genome that is reverse transcribed into DNA and then integrated into the cellular DNA. Once integrated, HTLV-1 continues to exist only as a provirus which can spread from cell to cell through a viral synapse. Few, if any, free virions are produced, and there is usually no detectable virus in the blood plasma though the virus is present in genital secretions. HTLV-1 predominately infects CD4+ T-lymphocytes and causes adult T-cell leukemia/lymphoma (ATLL)—a rare, yet aggressive hematological malignancy with high rates of therapy-resistance and generally poor clinical outcomes, in addition to several autoimmune/inflammatory conditions, including infectious dermatitis, rheumatoid arthritis, uveitis, keratoconjunctivitis, sicca syndrome, Sjögren's syndrome, and HAM/TSP, among others. HAM/TSP is clinically characterized by chronic progressive spastic paraparesis, urinary incontinence, and mild sensory disturbance. While ATLL is etiologically linked to viral latency, oncogenic transformation, and the clonal expansion of HTLV-1-infected cells, the inflammatory diseases, such as HTLV-1-associated myelopathy/tropical spastic paraparesis (HAM/TSP), are caused by autoimmune and/or immunopathological responses to proviral replication and the expression of viral antigens. HAM/TSP is a progressive neuroinflammatory disease that results in the deterioration and demyelination of the lower spinal cord. HTLV-1-infected circulating T-cells invade the central nervous system (CNS) and cause an immunopathogenic response against virus and possibly components of the CNS. Neural damage and subsequent degeneration can cause severe disability in patients with HAM/TSP. The persistence of proviral replication and the proliferation of HTLV-1-infected cells in the CNS leads to a cytotoxic T-cell response targeted against viral antigens, and which may be responsible for the autoimmune destruction of nervous tissues.

Even though cardiac glycosides have been demonstrated to exhibit some antiviral activity against a few viruses, the specific compounds exhibit very different levels of antiviral activity against different viruses, meaning that some exhibit very poor antiviral activity and some exhibit better antiviral activity when evaluated against the same virus(es).

A need remains for improved pharmaceutical compositions containing oleandrin, oleanolic acid, ursolic acid, betulinic acid or any combination thereof that are therapeutically active against specific viral infections.

SUMMARY OF THE INVENTION

The invention provides a pharmaceutical composition and method for treating viral infection in a mammalian subject. The invention also provides a pharmaceutical composition and method for treating viral infection, e.g. Viral hemorrhagic fever (VHF) infection, in a mammalian subject. The invention also provides a method of treating viral infection in mammals by administration of the pharmaceutical composition. The inventors have succeeded in preparing antiviral compositions that exhibit sufficient antiviral activity to justify their use in treating viral infection in humans and animals. The inventors have developed corresponding treatment methods employing particular dosing regimens.

In some embodiments, the viral infection is caused by any of the following virus families: Arenaviridae, Bunyaviridae, Filoviridae, Flaviviridae, Paramyxoviridae, Retroviridae (in particular, *Deltaretrovirus* genus), or Togaviridae.

Some embodiments of the invention are directed to compositions for and methods of treating Filovirus infection, *Flavivirus* infection, Henipavirus infection, alphavirus infection, or Togavirus infection. Viral infections that can be treated include, at least, Ebolavirus, Marburgvirus, Alphavirus, *Flavivirus*, Yellow Fever, Dengue Fever, Japanese Enchephalitis, West Nile Viruses, Zikavirus, Venezuelan Equine Encephalomyelitis (encephalitis) (VEE) virus, Chikungunya virus, Western Equine Encephalomyelitis (encephalitis) (WEE) virus, Eastern Equine Encephalomyelitis (encephalitis) (EEE) virus, Tick-borne Encephalitis, Kyasanur Forest Disease, Alkhurma Disease, Omsk Hemorrhagic Fever, Hendra virus, Nipah virus, *Deltaretrovirus* genus, HTLV-1 virus, and species thereof.

Some embodiments of the invention are directed to compositions for and methods of treating viral infections from viruses of the Filoviridae family, Flavivirudae family (*Flavivirus* genus), Paramyxoviridae family, Retroviridae family (*Deltaretrovirus* genus), or Togaviridae family.

Some embodiments of the invention are directed to compositions for and methods of treating viral infections from viruses of the Henipavirus genus, Ebolavirus genus, *Flavivirus* genus, Marburgvirus genus, *Deltaretrovirus* genus, or Alphavirus genus.

The invention also provides embodiments for the treatment of HTLV-1-associated condition or neuro-inflammatory disease. In some embodiments, the HTLV-1-associated condition or neuro-inflammatory disease is selected from the group consisting of myelopathy/tropical spastic paraparesis (HAM/TSP), adult T-cell leukemia/lymphoma (ATLL), autoimmune condition, inflammatory condition, infectious dermatitis, rheumatoid arthritis, uveitis, keratoconjunctivitis, sicca syndrome, Sjogren's syndrome, and *Strongyloides stercoralis*.

The invention also provides a method of inhibiting the infectivity of HTLV-1 particles released into the culture supernatants of treated cells and also reducing the intercellular transmission of HTLV-1 by inhibiting the Env-dependent formation of virological synapses, the method comprising administering to a subject in need thereof an effective amount of the antiviral composition.

In some embodiments, the invention provides an antiviral composition comprising (consisting essentially of): a) specific cardiac glycoside(s); b) plural triterpenes; or c) a combination of specific cardiac glycoside(s) and plural triterpenes.

One aspect of the invention provides a method of treating viral infection in a subject by chronic administration to the subject of an antiviral composition. The subject is treated by chronically administering to the subject a therapeutically effective amount (therapeutically relevant dose) of the composition, thereby providing relief of symptoms associated with the viral infection or amelioration of the viral infection. Administration of the composition to the subject can begin immediately after infection or any time within one day to 5 days after infection or at the earliest time after definite diagnosis of infection with virus.

Accordingly, the invention also provides a method of treating viral infection in a mammal, the method comprising administering to the mammal one or more therapeutically effective doses of the antiviral composition. One or more doses are administered on a daily, weekly or monthly basis. One or more doses per day can be administered.

The invention also provides a method of treating viral infection in a subject in need thereof, the method comprising:
determining whether or not the subject has a viral infection;
indicating administration of antiviral composition;
administering an initial dose of antiviral composition to the subject according to a prescribed initial dosing regimen for a period of time;
periodically determining the adequacy of subject's clinical response and/or therapeutic response to treatment with antiviral composition; and
if the subject's clinical response and/or therapeutic response is adequate, then continuing treatment with antiviral composition as needed until the desired clinical endpoint is achieved; or
if the subject's clinical response and/or therapeutic response are inadequate at the initial dose and initial dosing regimen, then escalating or deescalating the dose until the desired clinical response and/or therapeutic response in the subject is achieved.

Treatment of the subject with antiviral composition is continued as needed. The dose or dosing regimen can be adjusted as needed until the patient reaches the desired clinical endpoint(s) such as a reduction or alleviation of specific symptoms associated with the viral infecion. Determination of the adequacy of clinical response and/or therapeutic response can be conducted by a clinician familiar with viral infections.

The individual steps of the methods of the invention can be conducted at separate facilities or within the same facility.

The antiviral composition can be administered chronically, i.e. on a recurring basis, such as daily, every other day, every second day, every third day, every fourth day, every fifth day, every sixth day, weekly, every other week, every second week, every third week, monthly, bimonthly, semimonthly, every other month every second month, quarterly, every other quarter, trimesterly, seasonally, semi-annually and/or annually. The treatment period one or more weeks, one or more months, one or more quarters and/or one or more years. An effective dose of cardiac glycoside is administered one or more times in a day;

In some embodiments, the subject is administered 140 microg to 315 microg per day of cardiac glycoside. In some embodiments, a dose comprises 20 microg to 750 microg, 12 microg to 300 microg, or 12 microg to 120 microg of cardiac glycoside. The daily dose of cardiac glycoside can range from 20 microg to 750 microg, 0.01 microg to 100 mg, or 0.01 microg to 100 microg of cardiac glycoside/day. The recommended daily dose of oleandrin, present in the SCF extract, is generally about 0.25 to about 50 microg twice daily or about 0.9 to 5 microg twice daily or about every 12 hours. The dose can be about 0.5 to about 100 microg/day, about 1 to about 80 microg/day, about 1.5 to about 60 microg/day, about 1.8 to about 60 microg/day, about 1.8 to about 40 microg/day. The maximum tolerated dose can be about 100 microg/day, about 80 microg/day, about 60 microg/day, about 40 microg/day, about 38.4 microg/day or about 30 microg/day of oleander extract containing oleandrin and the minimum effective dose can be about 0.5 microg/day, about 1 microg/day, about 1.5 microg/day, about 1.8 microg/day, about 2 microg/day, or about 5 microg/day. Suitable doses comprising cardiac glycoside and triterpene can be about 0.05-0.5 mg/kg/day, about 0.05-0.35 mg/kg/day, about 0.05-0.22 mg/kg/day, about 0.05-0.4 mg/kg/day, about 0.05-0.3 mg/kg/day, about 0.05-0.5 microg/kg/day, about 0.05-0.35 microg/kg/day, about 0.05-0.22 microg/kg/day, about 0.05-0.4 microg/kg/day, or about 0.05-0.3 microg/kg/day.

The antiviral composition can be administered systemically. Modes of systemic administration include parenteral, buccal, enteral, intramuscular, subdermal, sublingual, peroral, or oral. The composition can also be administered via injection or intravenously.

If present in the antiviral composition, the cardiac glycoside is preferably oleandrin but can also include odoroside, neritaloside, or oleandrigenin. In some embodiments, the composition further comprises: a) one or more triterpenes; b) one or more steroids; c) one or more triterpene derivatives; d) one or more steroid derivatives; or e) a combination thereof. In some embodiments, the composition comprises cardiac glycoside and: a) two or three triterpenes; b) two or three triterpene derivatives; c) two or three triterpene salts; or d) a combination thereof. In some embodiments, the triterpene is selected from the group consisting of oleanolic acid, ursolic acid, betulinic acid and salts or derivatives thereof.

Some embodiments of the invention include those wherein a pharmaceutical composition comprises at least one pharmaceutical excipient and the antiviral composition. In some embodiments, the antiviral composition comprises: a) at least one cardiac glycoside and at least one triterpene; b) at least one cardiac glycoside and at least two triterpenes; c) at least one cardiac glycoside and at least three triterpenes; d) at least two triterpenes and excludes cardiac glycoside; e) at least three triterpenes and excludes cardiac glycoside; or f) at least one cardiac glycoside, e.g. oleandrin. As used herein, the generic terms triterpene and cardiac glycoside also encompass salts and derivatives thereof, unless otherwise specified.

The cardiac glycoside can be present in a pharmaceutical composition in pure form or as part of an extract containing one or more cardiac glycosides. The triterpene(s) can be present in a pharmaceutical composition in pure form or as part of an extract containing triterpene(s). In some embodiments, the cardiac glycoside is present as the primary therapeutic component, meaning the component primarily responsible for antiviral activity, in the pharmaceutical composition. In some embodiments, the triterpene(s) is/are present as the primary therapeutic component(s), meaning the component(s) primarily responsible for antiviral activity, in the pharmaceutical composition.

In some embodiments, an extract comprising the antiviral composition is obtained by extraction of plant material. The extract can comprise a hot-water extract, cold-water extract, supercritical fluid (SCF) extract, organic solvent extract, or combination thereof of the plant material. In some embodiments, the plant material is *Nerium* species or *Thevetia* species plant mass. Particular species include *Nerium oleander* or *Thevetia nerifolia*. In some embodiments, the extract comprises at least one other pharmacologically active agent, obtained along with the cardiac glycoside during extraction, that contributes to the therapeutic efficacy of the cardiac glycoside when the extract is administered to a subject. In some embodiments, the composition further comprises one or more other non-cardiac glycoside therapeutically effective agents, i.e. one or more agents that are not cardiac glycosides. In some embodiments, the composition further comprises one or more antiviral compound(s). In some embodiments, the antiviral composition excludes a pharmacologically active polysaccharide.

In some embodiments, the extract comprises one or more cardiac glycosides and one or more cardiac glycoside precursors (such as cardenolides, cardadienolides and cardatrienolides, all of which are the aglycone constituents of cardiac glycosides, for example, digitoxin, acetyl digitoxins, digitoxigenin, digoxin, acetyl digoxins, digoxigenin, medigoxin, strophanthins, cymarine, ouabain, or strophanthidin). The extract may further comprise one or more glycone constituents of cardiac glycosides (such as glucoside, fructoside, and/or glucuronide) as cardiac glycoside presursors. Accordingly, the antiviral composition may comprise one or more cardiac glycosides and two more cardiac glycoside precursors selected from the group consisting of one or more aglycone constituents, and one or more glycone constituents.

In some embodiments, a composition containing oleandrin (OL), oleanolic acid (OA), ursolic acid (UA) and betulinic acid (BA) is more efficacious than pure oleandrin, when equivalent doses based upon oleandrin content are compared.

In some embodiments, the molar ratio of total triterpene content (OA+UA+BA) to oleandrin ranges from about 15:1 to about 5:1, or about 12:1 to about 8:1, or about 100:1 to about 15:1, or about 100:1 to about 50:1, or about 100:1 to about 75:1, or about 100:1 to about 80:1, or about 100:1 to about 90:1, or about 10:1.

In some embodiments, the molar ratios of the individual triterpenes to oleandrin range as follows: about 2-8 (OA):about 2-8 (UA):about 0.1-1 (BA):about 0.5-1.5 (OL); or about 3-6 (OA):about 3-6 (UA):about 0.3-8 (BA):about 0.7-1.2 (OL); or about 4-5 (OA):about 4-5 (UA):about 0.4-0.7 (BA):about 0.9-1.1 (OL); or about 4.6 (OA):about 4.4 (UA):about 0.6 (BA):about 1 (OL).

In some embodiments, the other therapeutic agent is not a polysaccharide obtained during preparation of the extract, meaning it is not an acidic homopolygalacturonan or arabinogalaturonan. In some embodiments, the extract excludes another therapeutic agent and/or excludes an acidic homopolygalacturonan or arabinogalaturonan obtained during preparation of the extract.

The invention also provides use of a cardiac glycoside in the manufacture of a medicament for the treatment of viral infection in a subject. In some embodiments, the manufacture of such a medicament comprises: providing one or more antiviral compounds of the invention; including a dose of antiviral compound(s) in a pharmaceutical dosage form; and packaging the pharmaceutical dosage form. In some embodiments, the manufacture can be conducted as described in PCT International Application No. PCT/US06/29061. The manufacture can also include one or more additional steps such as: delivering the packaged dosage form to a vendor (retailer, wholesaler and/or distributor); selling or otherwise providing the packaged dosage form to a subject having a viral infection; including with the medicament a label and a package insert, which provides instructions on use, dosing regimen, administration, content and toxicology profile of the dosage form. In some embodiments, the treatment of viral infection comprises: determining that a subject has a viral infection; indicating administration of pharmaceutical dosage form to the subject according to a dosing regimen; administering to the subject one or more pharmaceutical dosage forms, wherein the one or more pharmaceutical dosage forms is administered according to the dosing regimen.

The pharmaceutical composition can further comprise a combination of at least one material selected from the group consisting of a water soluble (miscible) co-solvent, a water insoluble (immiscible) co-solvent, a surfactant, an antioxidant, a chelating agent, and an absorption enhancer.

The solubilizer is at least a single surfactant, but it can also be a combination of materials such as a combination of: a) surfactant and water miscible solvent; b) surfactant and water immiscible solvent; c) surfactant, antioxidant; d) surfactant, antioxidant, and water miscible solvent; e) surfactant, antioxidant, and water immiscible solvent; f) surfactant, water miscible solvent, and water immiscible solvent; or g) surfactant, antioxidant, water miscible solvent, and water immiscible solvent.

The pharmaceutical composition optionally further comprises: a) at least one liquid carrier; b) at least one emulsifying agent; c) at least one solubilizing agent; d) at least one dispersing agent; e) at least one other excipient; or f) a combination thereof.

In some embodiments, the water miscible solvent is low molecular weight (less than 6000) PEG, glycol, or alcohol. In some embodiments, the surfactant is a pegylated surfactant, meaning a surfactant comprising a poly(ethylene glycol) functional group.

The invention includes all combinations of the aspects, embodiments and sub-embodiments of the invention disclosed herein.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

FIGS. 1-2 depict charts summarizing the in vitro dose response antiviral activity of various compositions against Ebolavirus.

FIGS. 3-4 depict charts summarizing the in vitro dose response antiviral activity of various compositions against Marburgvirus.

FIG. 10A—2 hr post-infection; FIG. 10B—24 hr post-infection.

FIG. 11A—2 hr post-infection; FIG. 11B—24 hr post-infection.

FIG. 12A—Ebolavirus; FIG. 12B—Marburgvirus.

FIG. 14 depicts a chart summarizing the effect that vehicle control, oleandrin, or extract of $N.$ $oleander$ have upon HTLV-1 replication or the release of newly-synthesized virus particles as determined by quantitation of HTLV-1 $p19^{Gag}$ (see Examples 19 and 20). Untreated (UT) cells are shown for comparison. All the data is representative of at least three independent experiments. The data represent the mean of the experiments±standard deviation (error bars).

FIG. 15 depicts a chart summarizing the relative cytotoxicity of the Vehicle control, oleandrin, and $N.$ $oleander$ extract against the HTLV-1+ SLB1 lymphoma T-cell-line. All the data is representative of at least three independent experiments. The data represent the mean of the experiments±standard deviation (error bars).

FIG. 17 depicts a chart summarizing the effect that vehicle control, oleandrin, or extract of $N.$ $oleander$ have upon HTLV-1 replication or the release of newly-synthesized virus particles from oleandrin-treated HTLV-1+ lymphoma T-cells.

FIG. 18 depicts a chart summarizing the relative cytotoxicity of vehicle control, oleandrin, or extract of $N.$ $oleander$ upon treated huPBMCs.

FIG. 19 depicts a chart summarizing the relative inhibition of HTLV-1 transmission in co-culture assays huPBMCs containing vehicle control, oleandrin, or extract of $N.$ $oleander$.

FIG. 20 depicts representative micrographs of a GFP-expressing HTLV-1+ SLB1 T-cell-line: fluorescence-microscopy (top panels) and immunoblotting (lower panels).

FIG. 21 depicts representative micrographs of virological synapses between huPBMCs and the mitomycin C-treated HTLV-1+ SLB1/pLenti-GFP lymphoblasts (green cells).

FIG. 22 depicts a chart of the averaged data with standard deviation (error bars) from quantitation of the micrographs of FIG. 21.

DETAILED DESCRIPTION OF THE INVENTION

Figure 5:
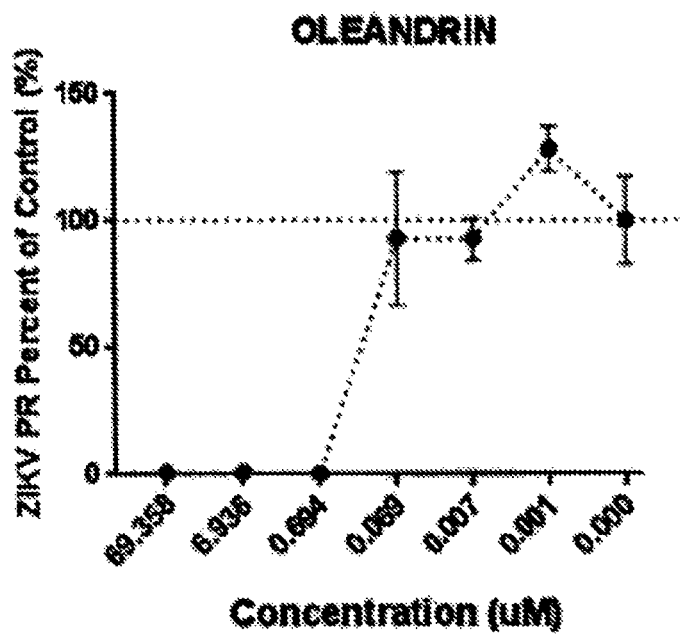
FIG. 5 depicts a chart summarizing the in vitro dose response antiviral activity of oleandrin against Zikavirus (SIKV strain PRVABC59) in Vero E6 cells.

The invention provides a method of treating viral infection in a subject by chronic administration of an effective dose of antiviral composition (or pharmaceutical composition comprising the antiviral composition and at least one pharmaceutical excipient) to the subject. The pharmaceutical composition is administered according to a dosing regimen best suited for the subject, the suitability of the dose and dosing regimen to be determined clinically according to conventional clinical practices and clinical treatment endpoints for viral infection.

As used herein, the term "subject" is taken to mean warm blooded animals such as mammals, for example, cats, dogs, mice, guinea pigs, horses, bovine cows, sheep, and humans.

As used herein, a subject at risk of viral infection is: a) a subject living in a geographical area within which mosquitoes, in particular Aedes species (Aedes egypti, Aedes albopictus) mosquitoes, live; b) a subject living with or near a person or people having viral infection; c) a subject having sexual relations with a person having a viral infection; d) a subject living in a geographical area within which ticks, in particular Ixodes species (Ixodes marx, Ixodes scapularis, or Ixodes cooke species) ticks, live; e) a subject living in a geographical area within which fruit bats live; f) subjects living in a tropical region; g) subjects living in Africa; h) subjects in contact with bodily fluids of other subjects having a viral infection; i) a child; or j) a subject with a weakened immune system. In some embodiments, the subject is a female, a female capable of getting pregnant, or a pregnant female.

A subject treated according to the invention will exhibit a therapeutic response. By "therapeutic response" is meant that a subject suffering from the viral infection will enjoy at least one of the following clinical benefits as a result of treatment with a cardiac glycoside: reduction of the active viral titre in the subject's blood or plasma, eradication of active virus from the subject's blood or plasma, amelioration of the infection, reduction in the occurrence of symptoms associated with the infection, partial or full remission of the infection or increased time to progression of the infection, and/or reduction in the infectivity of the virus causing said viral infection. The therapeutic response can be a full or partial therapeutic response.

As used herein, "time to progression" is the period, length or duration of time after viral infection is diagnosed (or treated) until the infection begins to worsen. It is the period of time during which the level of infection is maintained without further progression of the infection, and the period of time ends when the infection begins to progress again. Progression of a disease is determined by "staging" a subject suffering from the infection prior to or at initiation of therapy. For example, the subject's health is determined prior to or at initiation of therapy. The subject is then treated with antiviral composition, and the viral titre is monitored periodically. At some later point in time, the symptoms of the infection may worsen, thus marking progression of the infection and the end of the "time to progression". The period of time during which the infection did not progress or during which the level or severity of the infection did not worsen is the "time to progression".

A dosing regimen includes a therapeutically relevant dose (or effective dose) of one or more cardiac glycosides, and/or triterpene(s), administered according to a dosing schedule. A therapeutically relevant dose, therefore, is a therapeutic dose at which a therapeutic response of the viral infection to treatment with antiviral composition is observed and at which a subject can be administered the antiviral composition without an excessive amount of unwanted or deleterious side effects. A therapeutically relevant dose is non-lethal to a subject, even though it may cause some side effects in the patient. It is a dose at which the level of clinical benefit to a subject being administered the antiviral composition exceeds the level of deleterious side effects experienced by the subject due to administration of the antiviral composition or component(s) thereof. A therapeutically relevant dose will vary from subject to subject according to a variety of established pharmacologic, pharmacodynamic and pharmacokinetic principles. However, a therapeutically relevant dose (relative, for example, to oleandrin) will typically be about about 25 micrograms, about 100 micrograms, about 250 micrograms, about 500 micrograms or about 750 micrograms of cardiac glycoside/day or it can be in the range of about 25-750 micrograms of cardiac glycoside per dose, or might not exceed about 25 micrograms, about 100 micrograms, about 250 micrograms, about 500 micrograms or about 750 micrograms of cardiac glycoside/day. Another example of a therapeutically relevant dose (relative, for example, to triterpene either individually or together) will typically be in the range of about 0.1 micrograms to 100 micrograms, about 0.1 mg to about 500 mg, about 100 to about 1000 mg per kg of body weight, about 15 to about 25 mg/kg, about 25 to about 50 mg/kg, about 50 to about 100 mg/kg, about 100 to about 200 mg/kg, about 200 to about 500 mg/kg, about 10 to about 750 mg/kg, about 16 to about 640 mg/kg, about 15 to about 750 mg/kg, about 15 to about 700 mg/kg, or about 15 to about 650 mg/kg of body weight. It is known in the art that the actual amount of antiviral composition required to provide a target therapeutic result in a subject may vary from subject to subject according to the basic principles of pharmacy.

A therapeutically relevant dose can be administered according to any dosing regimen typically used in the treatment of viral infection. A therapeutically relevant dose can be administered once, twice, thrice or more daily. It can be administered every other day, every third day, every fourth day, every fifth day, semiweekly, weekly, biweekly, every three weeks, every four weeks, monthly, bimonthly, semimonthly, every three months, every four months, semiannually, annually, or according to a combination of any of the above to arrive at a suitable dosing schedule. For example, a therapeutically relevant dose can be administered one or more times daily (up to 10 times daily for the highest dose) for one or more weeks.

Figures 1, 2:
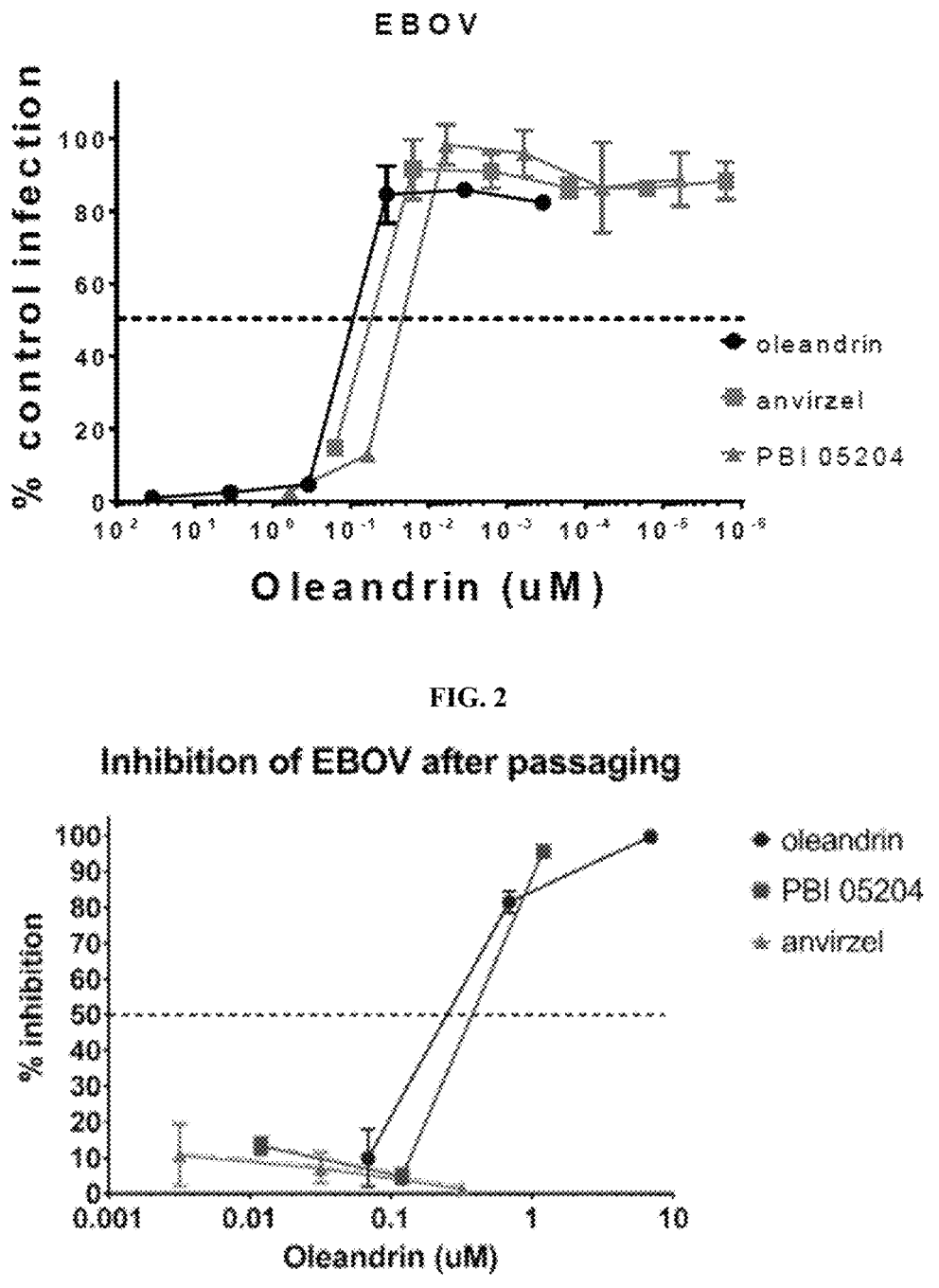

Example 15 provides a detailed description of an in vitro assay used to evaluate the efficacy of compositions containing oleandrin (as sole active), Anvirzel and PBI-05204 (supercritical fluid (SCF) extract of Nerium oleander) for the treatment of Ebolavirus (FIGS. 1-2) and Marburgvirus (FIGS. 3-4) infection, both of which are Filoviruses.

The experiments were set up by adding the compositions to cells at 40 microg/mL, then adding virus and incubating for 1 hr. Upon addition of the virus to the cells, the final concentration of the compositions is 20 microg/mL. Compositions containing different amounts of oleandrin can be adjusted according to the concentration of oleandrin they contain, and converted that to molarity. FIGS. 1-4 depict the efficacy based on the oleandrin content of the extracts. OL on its own is efficacious. PBI-05204, the SCF extract of *Nerium oleander* comprising OL, OA, UA and BA, is substantially more efficacious than OL on its own. Anvirzel, the hot water extract of *Nerium oleander*, is more efficacious than OL on its own. Both extracts clearly exhibit efficacy in the nanomolar range. The percentage of oleandrin in the PBI-05204 extract (1.74%) is higher than in Anvirzel (0.459%, 4.59 microg/mg). At the highest dose of PBI-05204, it completely inhibited EBOV and MARV infection, whereas Anvirzel did not exhibit complete inhibition, because at a dose higher than 20 microg/mL with anvirzel, toxicity is observed. The data demonstrate highest antiviral activity against Ebolavirus and Marburgvirus for PBI-05204. The combination of triterpenes in PBI-05204 increased the antiviral activity of oleandrin.

Figure 6:
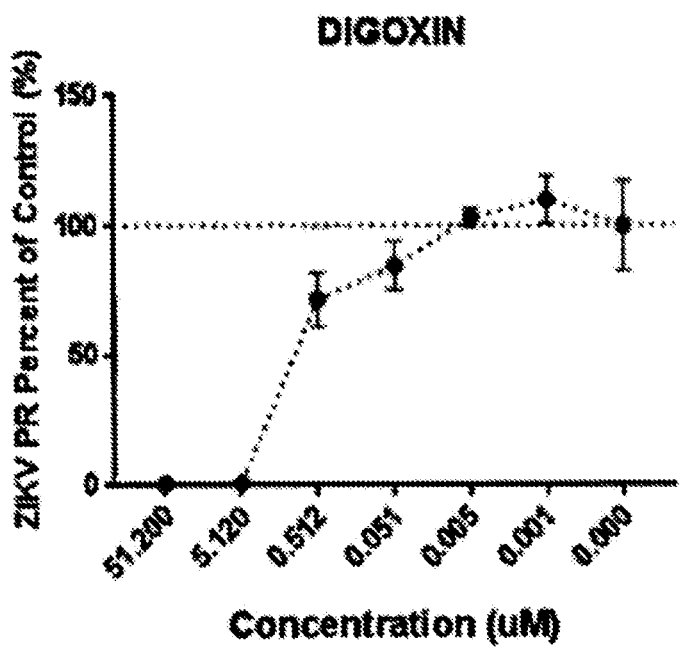
FIG. 6 depicts a chart summarizing the in vitro dose response antiviral activity of digoxin against Zikavirus (SIKV strain PRVABC59) in Vero E6 cells.

Example 6 provides a detailed description of an in vitro assay used to evaluate the efficacy of the cardiac glycosides for the treatment of Zikavirus (a flavivirus) infection. Vero E6 cells were infected with Zika virus (ZIKV strain PRV-ABC59) at an MOI of 0.2 in the presence of oleandrin (FIG. 5) or digoxin (FIG. 6). The cells were incubated with virus and the cardiac glycoside for 1 hr, after which the inoculum and non-absorbed cardiac glycoside (if any) was removed. The cells were immersed in fresh medium and incubated for 48 hr, after which they were fixed with formalin and stained for ZIKV infection. The data demonstrate antiviral activity against Zikavirus for both cardiac glycosides; however, oleandrin exhibited higher (almost 8-fold greater) antiviral activity than digoxin.

Example 14 provides a detailed description of an assay used to evaluate the antiviral activity of test compositions against Zikavirus and Dengue virus. The data indicate that oleandrin demonstrates efficacy against Zikavirus and Dengue virus.

Figure 7:
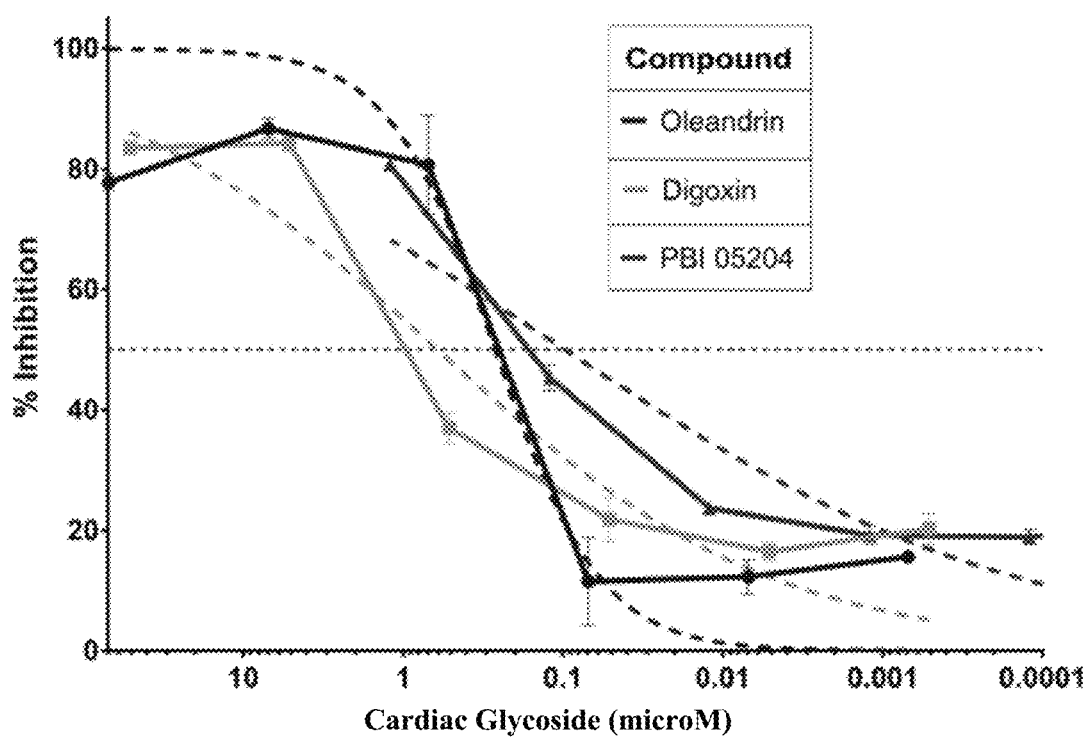
FIG. 7 depicts a chart summarizing the in vitro dose response antiviral activity of various compositions (oleandrin, digoxin and PBI-05204) against Ebolavirus in Vero E6 cells.
Figure 8:
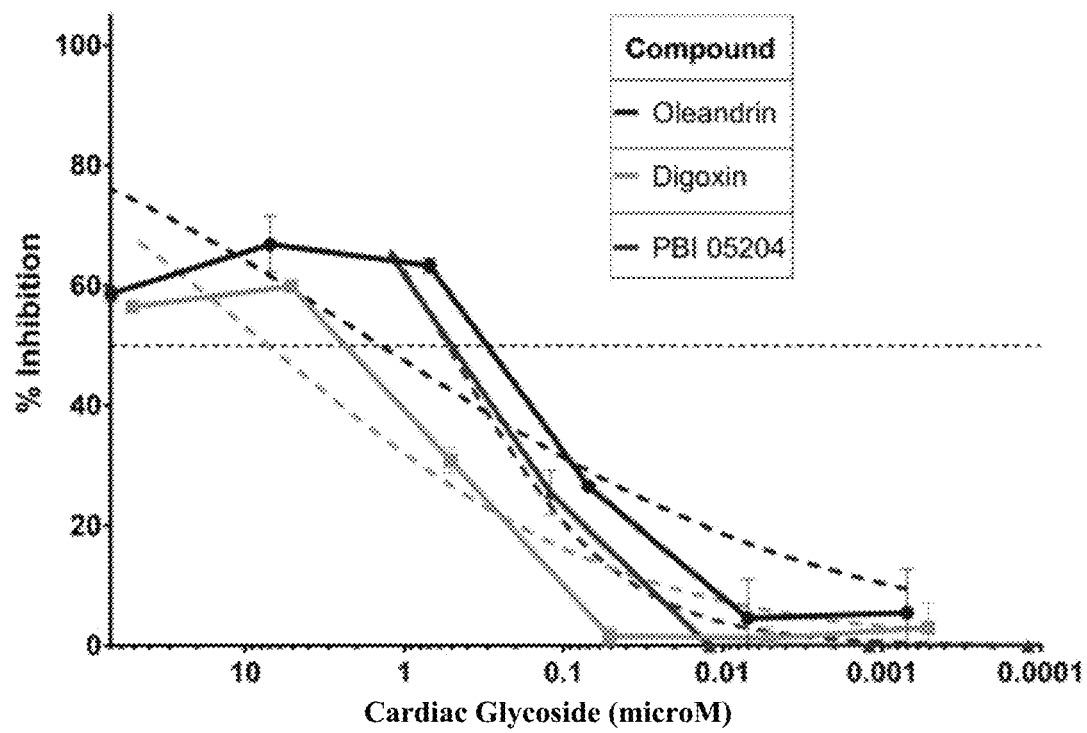
FIG. 8 depicts a chart summarizing the in vitro dose response antiviral activity of various compositions (oleandrin, digoxin and PBI-05204) against Marburgvirus in Vero E6 cells.
Figure 9:
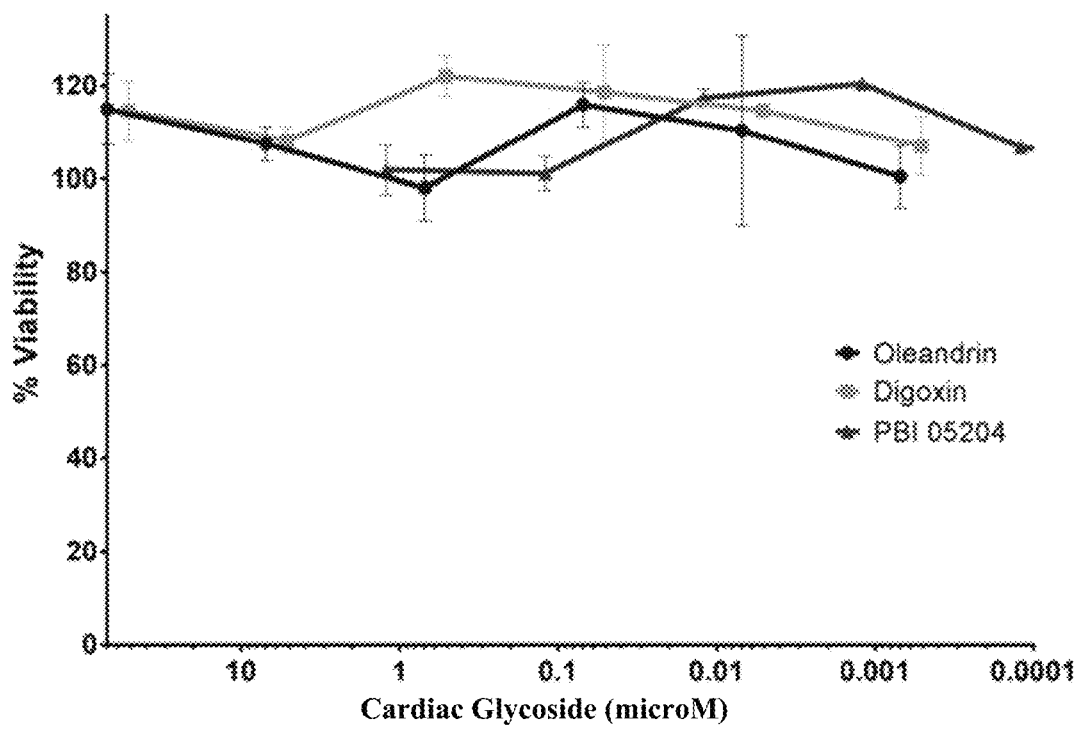
FIG. 9 depicts a chart summarizing the in vitro cellular viability of Vero E6 cells in the presence of various compositions (oleandrin, digoxin and PBI-05204).

FIG. 7 a chart summarizing the in vitro dose response antiviral activity of various compositions (oleandrin, digoxin and PBI-05204) against Ebolavirus (EBOV) in Vero E6 cells. FIG. 8 depicts a chart summarizing the in vitro dose response antiviral activity of various compositions (oleandrin, digoxin and PBI-05204) against Marburgvirus (MARV) in Vero E6 cells. FIG. 9 depicts a chart summarizing the in vitro cellular viability of Vero E6 cells in the presence of various compositions (oleandrin, digoxin and PBI-05204). For FIGS. 7-8, the host cells were exposed to the compositions prior to infection with virus. Vero E6 cells were infected with EBOV/Kik (FIG. 7, MOI=1) or MARV/Ci67 (FIG. 8, MOI=1) in the presence of oleandrin, digoxin or PBI-05204, an oleandrin-containing plant extract. After 1 hr, inoculum and compounds were removed and fresh medium added to cells. 48 hr later, cells were fixed and immunostained to detect cells infected with EBOV or MARV. Infected cells were enumerated using an Operetta.

In order to ensure that false positives, in terms of antiviral activity, were not being observed, cellular viability in the presence of the compositions was tested. For the data in FIG. 9, Vero E6 cells were treated with compound as above. ATP levels were measured by CellTiter-Glo as a measurement of cell viability. It was determined that oleandrin, digoxin, and PBI-05204 did not reduce cellular viability, meaning that the antiviral activity detailed in other figures herein is not due to false positives caused by cellular toxicity of the individual compounds.

Accordingly, the invention provides a method of treating viral infection in a mammal or host cell, the method comprising: administering an antiviral composition to the mammal or host cell prior to contraction of said viral infection, whereby upon viral infection of said mammal or host cell, the antiviral composition reduces the viral titre and ameliorates, reduces or eliminates the viral infection.

The antiviral composition and method of the invention are also useful in treating viral infection that has occurred prior to administration of the antiviral composition. Vero E6 cells were infected with EBOV (FIGS. 10A, 10B) or MARV (FIGS. 11A, 11B). At 2 hr post-infection (FIGS. 10A, 11A) or 24 hr post-infection (FIGS. 10B, 11B), oleandrin or PBI-05204 was added to cells for 1 hr, then discarded and cells were returned to culture medium.

Figure 10A:
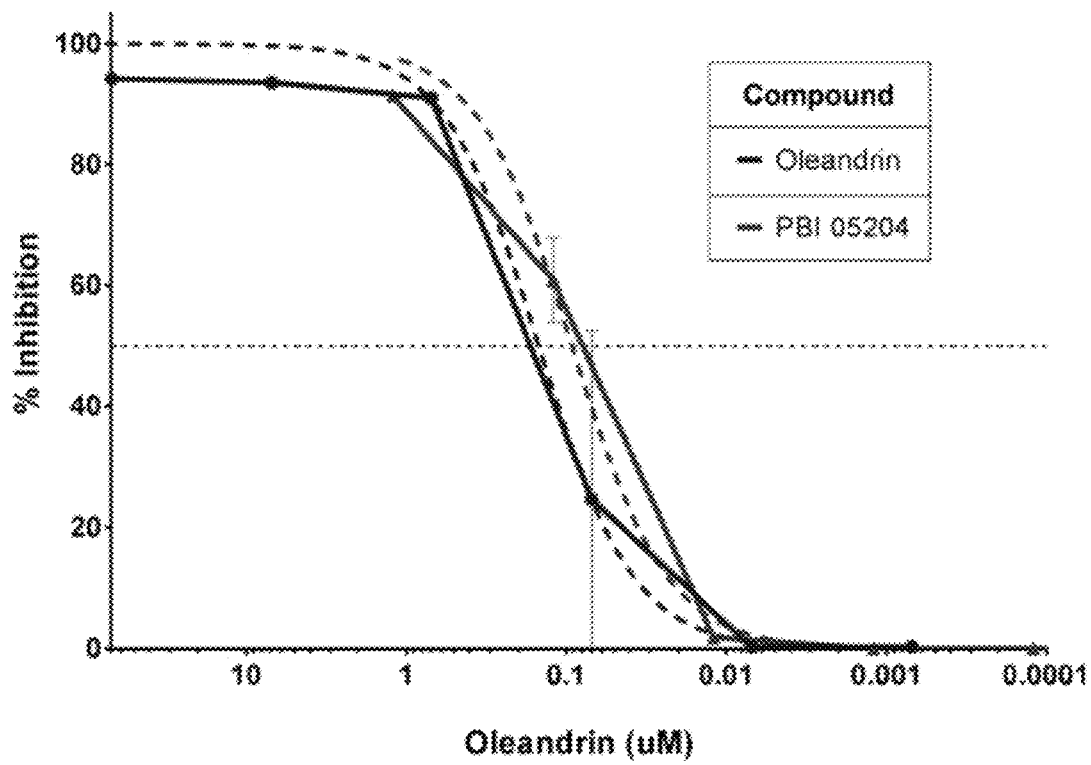
FIGS. 10A and 10B depict charts summarizing the ability of compositions (oleandrin and PBI-05204) to inhibit Ebolavirus in Vero E6 cells shortly after exposure to virus.
Figure 10B:
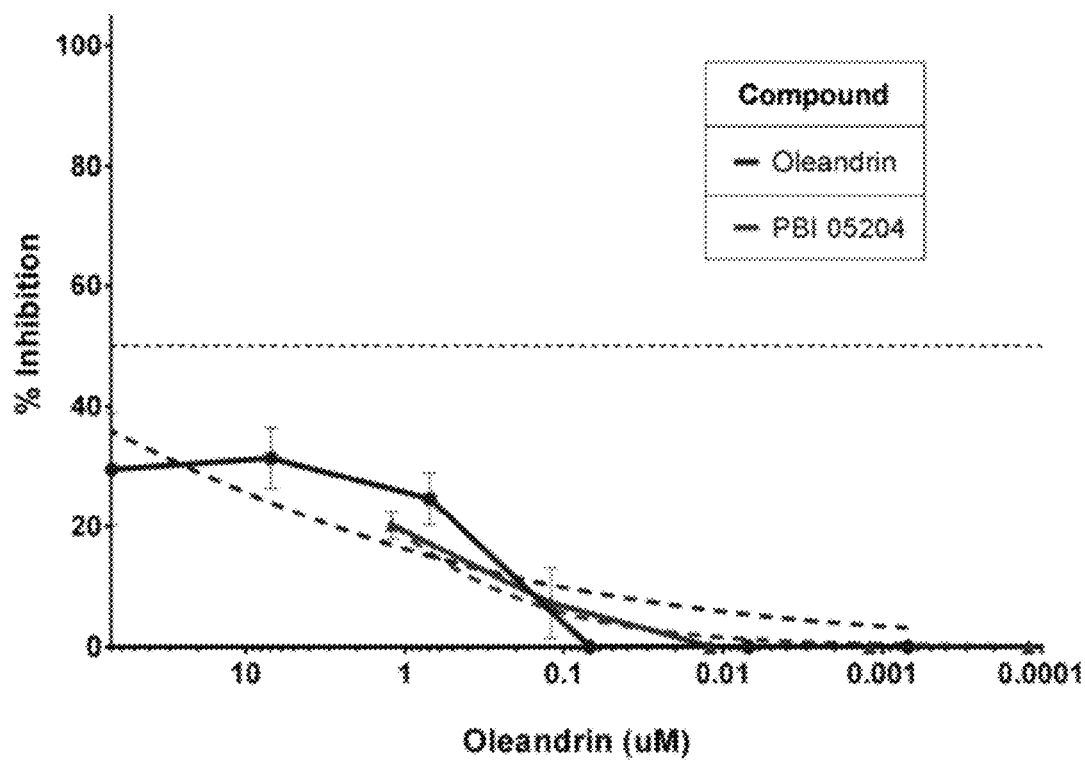
Figure 11A:
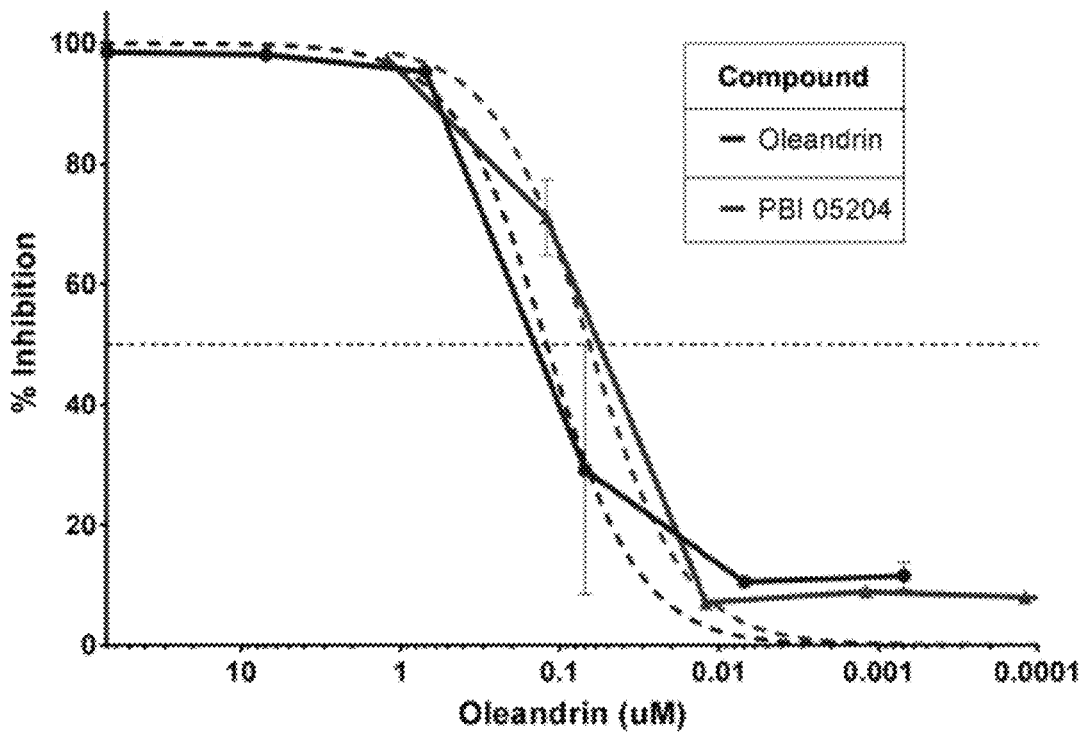
FIGS. 11A and 11B depict charts summarizing the ability of compositions (oleandrin and PBI-05204) to inhibit Marburgvirus in Vero E6 cells shortly after exposure to virus.
Figure 11B:
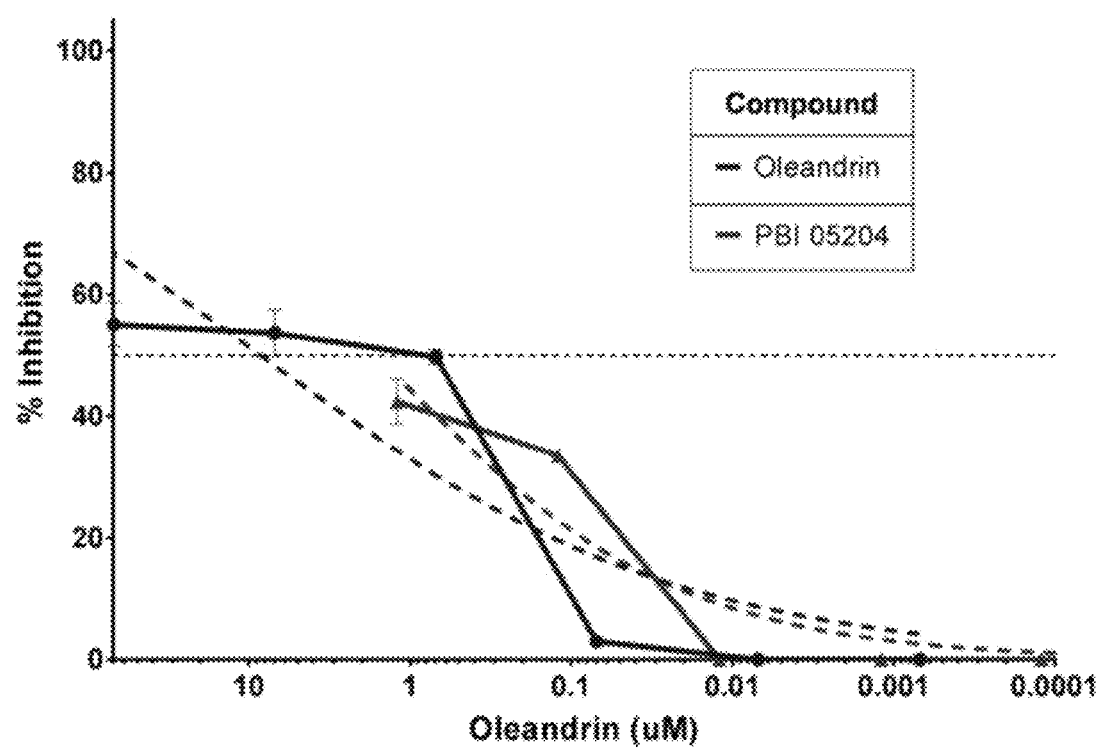
Figure 12A:
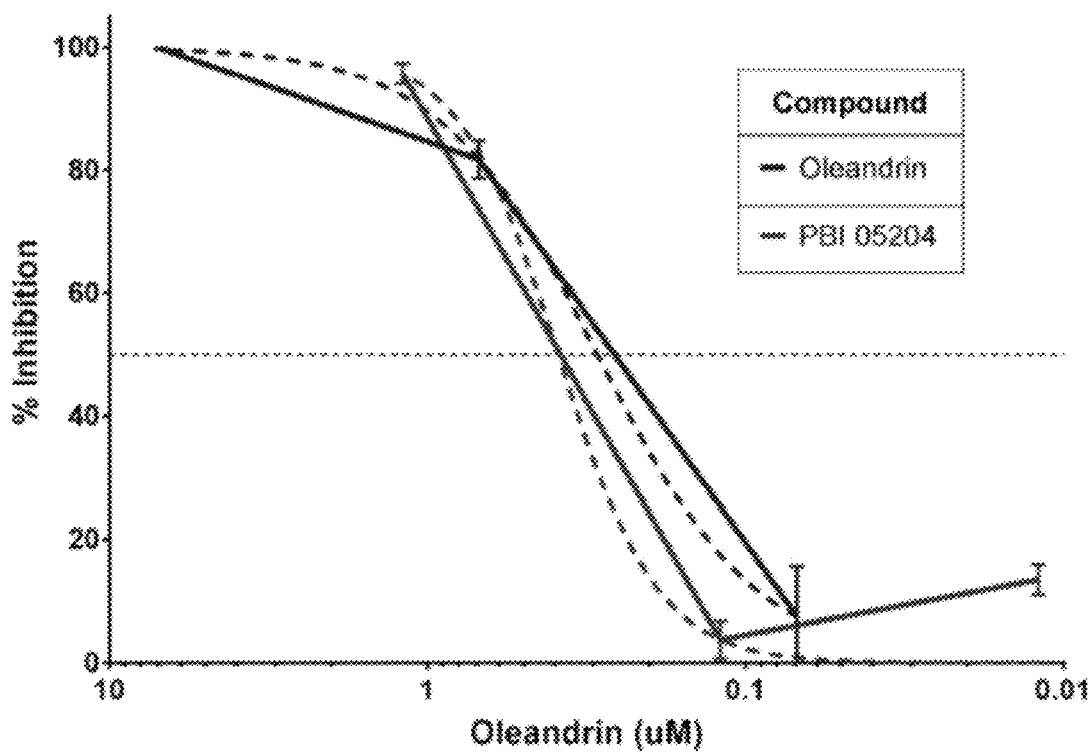
FIGS. 12A and 12B depict charts summarizing the ability of compositions (oleandrin and PBI-05204) to inhibit the product of infectious progeny by virally infected Vero E6 cells having been exposed to oleandrin.
Figure 12B:
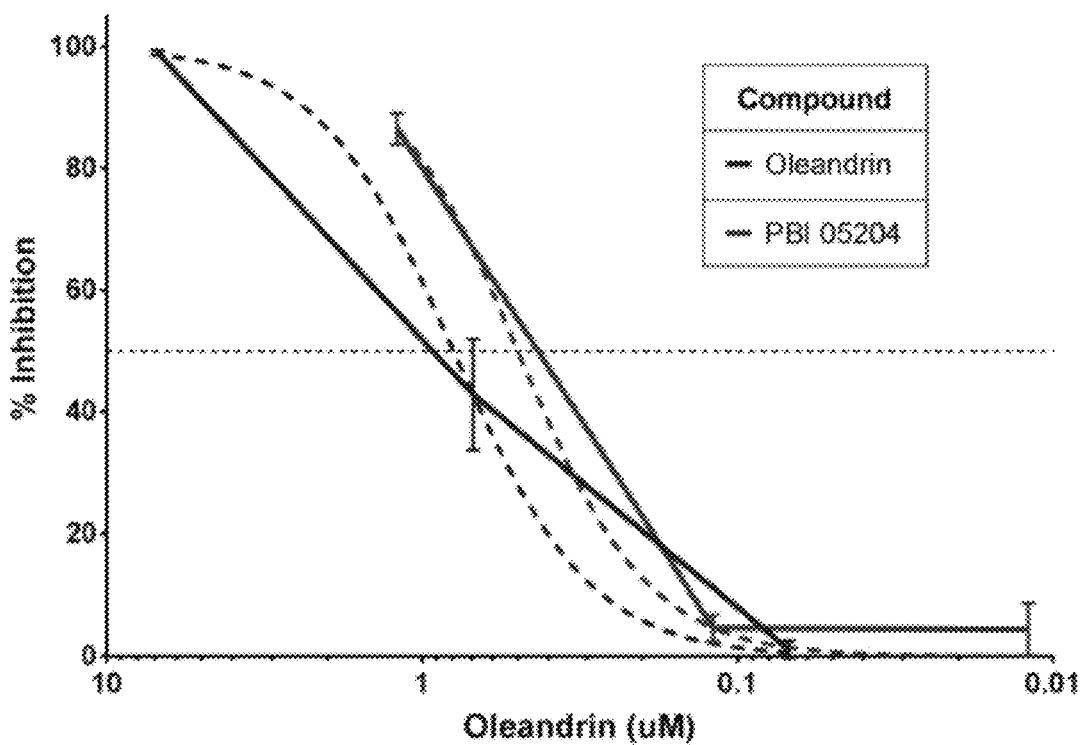

FIGS. 10A and 10B depict charts summarizing the ability of compositions (oleandrin and PBI-05204) to inhibit Ebolavirus in Vero E6 cells shortly after exposure to virus: FIG. 10A—2 hr post-infection; FIG. 10B—24 hr post-infection. When the antiviral composition is administered within two hours (or within up to 12 hours) after viral infection, the viral titre antiviral composition provides effective treatment and reduces the EBOV viral titre. Even after 24 hours, the viral composition is effective; however, its efficacy is lower as time after initial viral infection increases. The same evaluations were conducted on MARV. FIGS. 11A and 11B depict charts summarizing the ability of compositions (oleandrin and PBI-05204) to inhibit Marburgvirus in Vero E6 cells shortly after exposure to virus: FIG. 11A—2 hr post-infection; FIG. 11B—24 hr post-infection. When the antiviral composition is administered within two hours (or within up to 12 hours) after viral infection, the viral titre antiviral composition provides effective treatment and reduces the MARV viral titre. Even after 24 hours, the viral composition is effective; however, its efficacy is lower as time after initial viral infection increases.

Given that the antiviral activity of the composition herein is reduced for a single generation of virus-infected cells, e.g. within 24 hours post-infection, we evaluated whether the antiviral composition is capable of inhibiting viral propagation, meaning inhibiting production of infectious progeny. Vero E6 cells were infected with EBOV or MARV in the presence of oleandrin or PBI-05204 and incubated for 48 hr. Supernatants from infected cell cultures were passaged onto fresh Vero E6 cells, incubated for 1 hr, then discarded. Cells containing passaged supernatant were incubated for 48 hr. Cells infected with EBOV (B) or MARV (C) were evaluated as described herein. Control infection rates were 66% for EBOV and 67% for MARV. The antiviral composition of the invention inhibited production of infectious progeny.

Accordingly, the antiviral composition of the invention: a) can be administered prophylactically before viral infection to inhibit viral infection after exposure to virus; b) can be administered after viral infection to inhibit or reduce viral replication and production of infectious progeny; or c) a combination of a) and b).

Figure 13A:
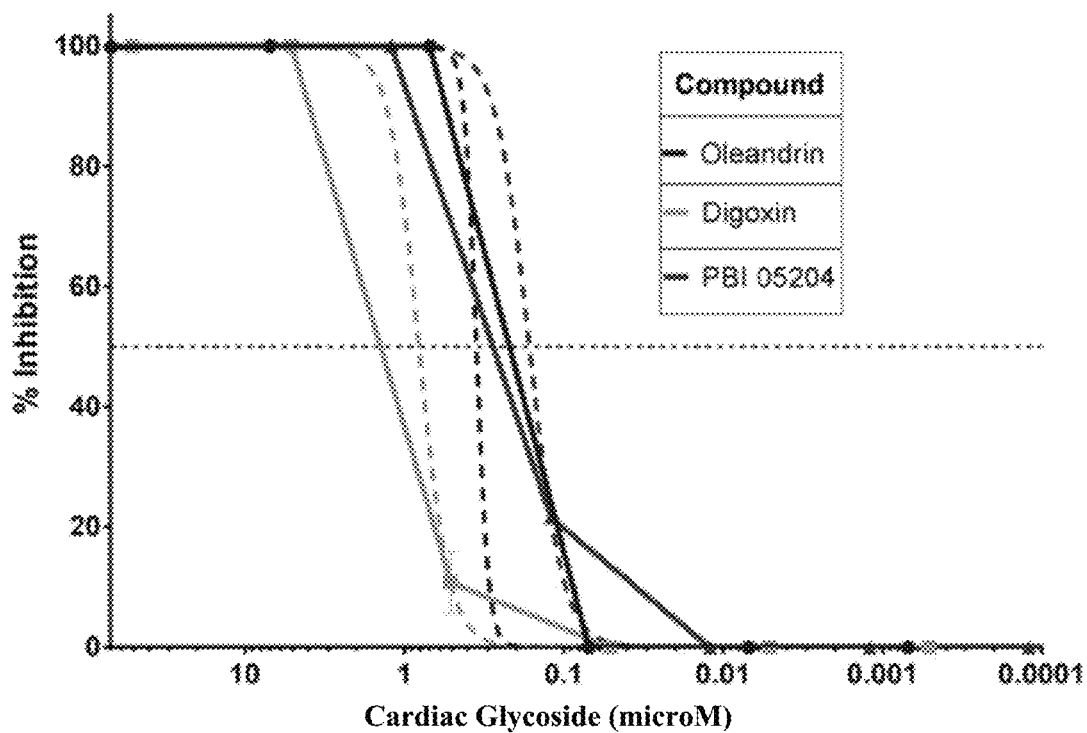
FIGS. 13A and 13B depict charts summarizing the in vitro dose response antiviral activity of various compositions (oleandrin, digoxin and PBI-05204) against Venezuelen Equine Encephalomyelits virus (FIG. 13A) and Western Equine Encephalomyelitis virus (FIG. 13B) in Vero E6 cells.
Figure 13B:
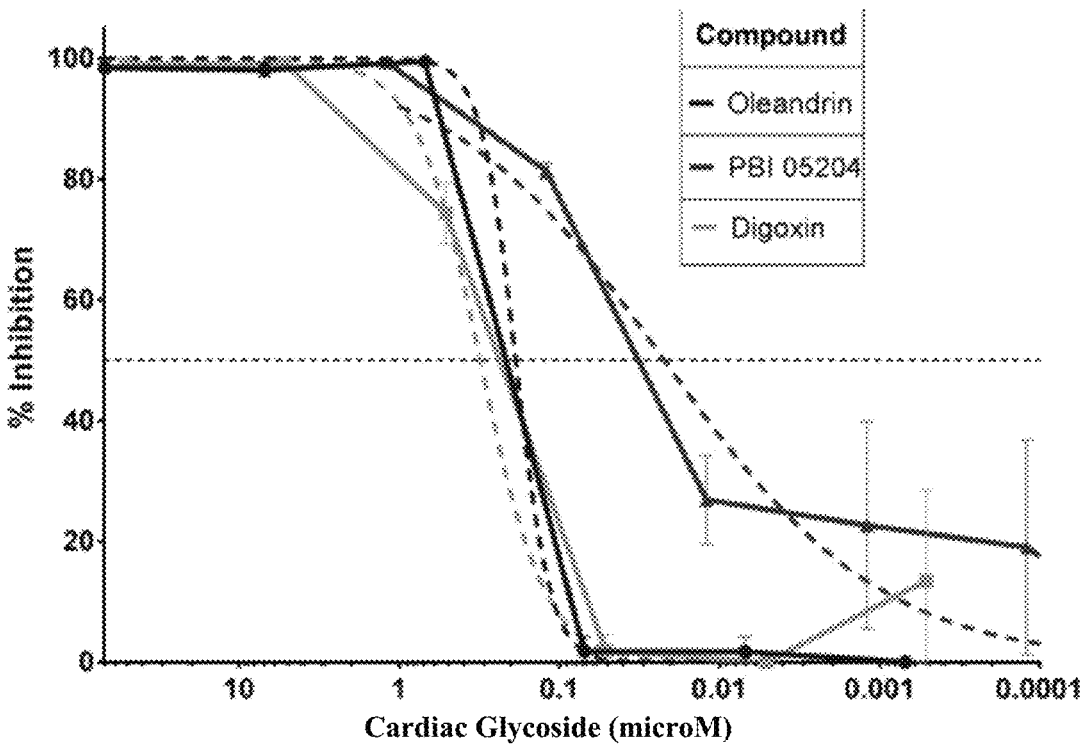

Antiviral activity of the antiviral composition against Togaviridae alphavirus was evaluated using VEE virus and WEE virus in Vero E6 cells. FIGS. 13A and 13B depict charts summarizing the in vitro dose response antiviral activity of various compositions (oleandrin, digoxin and PBI-05204) against Venezuelen Equine Encephalomyelits virus (FIG. 13A) and Western Equine Encephalomyelitis virus (FIG. 13B) in Vero E6 cells. Vero E6 cells were infected with Venezuelan equine encephalitis virus (FIG. 13A, MOI=0.01) or Western equine encephalitis virus (FIG. 13B, MOI=0.1) for 18 hr in the presence or absence of indicated compounds. Infected cells were detected as before and enumerated on an Operetta. The antiviral composition of the invention was found to be efficacious.

Accordingly, the invention provides a method of treating a viral infection, caused by a Filoviridae family virus, Flaviviridae family virus (*Flavivirus* genus), *Deltaretrovirus* genus virus, or Togaviridae family virus, in a subject or host cell, the method comprising administering an effective amount of the antiviral composition, thereby exposing the virus to the antiviral composition and treating said viral infection.

We evaluated use of oleandrin and the extract described herein for the treatment of HTLV-1 (human T-cell leukemia virus type-1; an enveloped retrovirus; *Deltaretrovirus* genus) infection. To determine whether the purified oleandrin compound, or an extract of *N. oleander*, could inhibit HTLV-1 proviral replication and/or the production and release of $p19^{Gag}$-containing virus particles, the virus-producing HTLV-1-transformed SLB1 lymphoma T-cell-line was treated with increasing concentrations of oleandrin or a *N. oleander* extract, or the sterile vehicle control (20% DMSO in MilliQ-treated ddH$_2$O) and then incubated for 72 hrs at 37.0 under 10% CO$_2$. The cells were later pelleted by centrifugation and the relative levels of extracellular $p19^{Gag}$-containing virus particles released into the culture supernatants were quantified by performing Anti-HTLV-1 $p19^{Gag}$ ELISAs (Zeptometrix).

Figure 14:
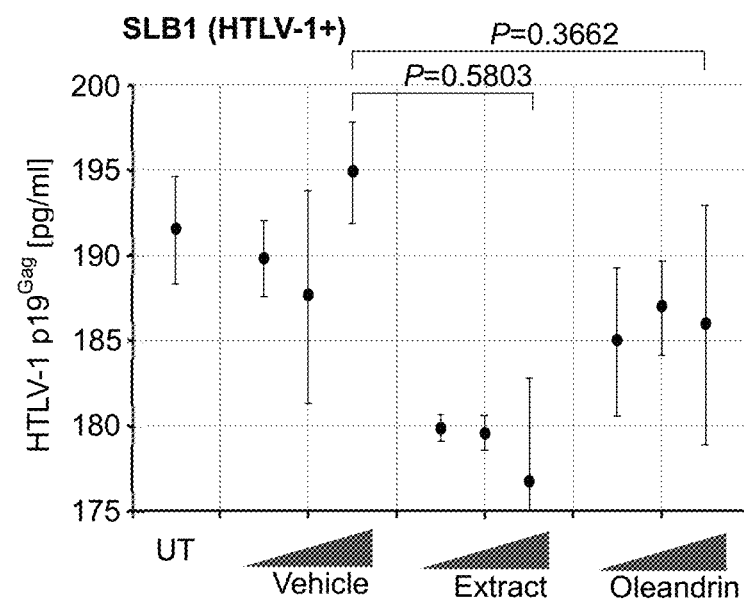
Figure 15:
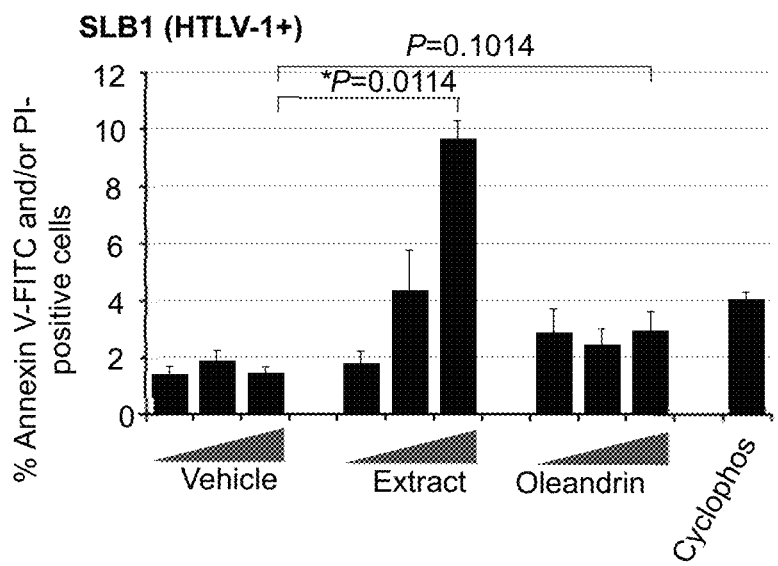
Figure 16A:
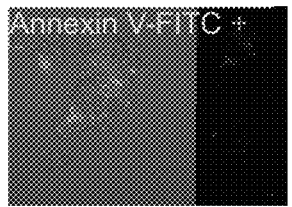
FIGS. 16A-16F depict representative micrographs of the Annexin V-FITC (green) and PI (red)-staining results with DIC phase-contrast in the merged images are shown. The individual Annexin V-FITC and PI fluorescent channel images are also provided. Scale bar, 20 μm.
Figure 16B:
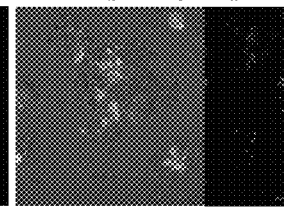
Figure 16C:
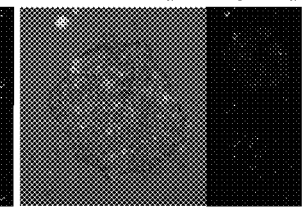
Figure 16D:
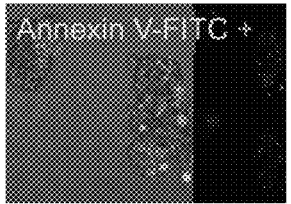
Figure 16E:
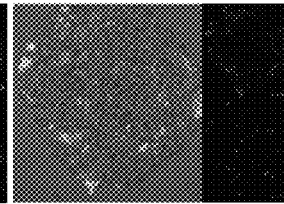
Figure 16F:
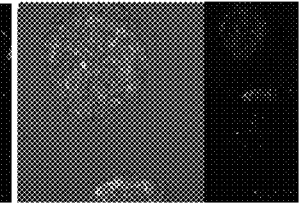
Figure 17:
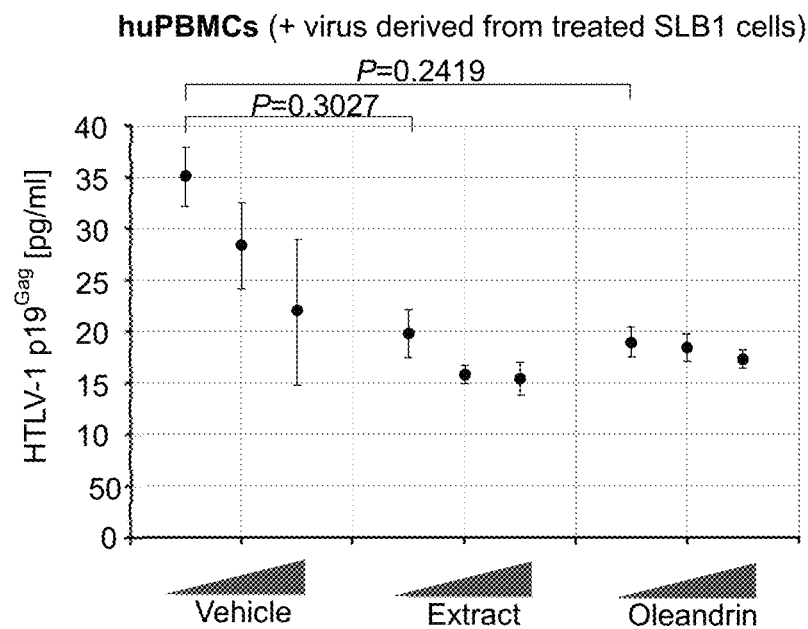
Figure 18:
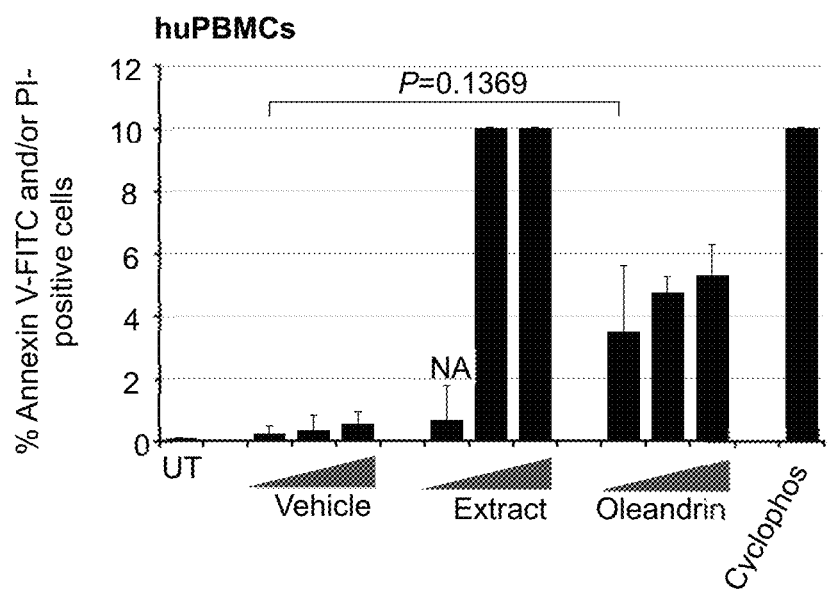

FIG. 14 depicts data for quantitation of HTLV-1 $p19^{Gag}$ expressed by HTLV-1+ SLB1 lymphoma T-cell-line treated for 72 hrs with the vehicle control (1.5 µl, 7.5 µl, or 15 µl), or increasing concentrations (10 µg/ml, 50 µg/ml, and 100 µg/ml) of the oleandrin compound or an extract of *N. oleander* (Example 19 and 20). Viral replication and the release of extracellular particles into the culture supernatants were quantified by performing Anti-HTLV-1 $p19^{Gag}$ ELISAs (Zeptometrix). Oleandrin does not significantly inhibit HTLV-1 replication or the release of newly-synthesized virus particles. We determined that neither the extract nor oleandrin alone significantly inhibit viral replication or the release of $p19^{Gag}$-containing particles into the supernatants of the cultures. We, thus, expected no further antiviral activity; however, we unexpectedly found that the collected virus particles from treated cells exhibited reduced infectivity on primary human peripheral blood mononuclear cells (huPBMCs). Unlike HIV-1, extracellular HTLV-1 particles are poorly infectious and viral transmission typically occurs via direct intercellular interactions across a virological synapse.

The invention thus provides a method of producing HTLV-1 virus particles with reduced infectivity, the method comprising treating HTLV-1 virus particles with the antiviral composition of the invention to provide said HTLV-1 virus particles with reduced infectivity.

To ensure that the antiviral activity observed was not an artifact due to potential cytotoxicity of the antiviral composition to HTLV-1+ SLB1 lymphoblast, we then assessed the cytotoxicity of the different dilutions of the purified oleandrin compound and *N. oleander* extract in treated HTLV-1+ SLB1 lymphoblast cultures (Example 21). SLB1 T-cells were treated with increasing concentrations (10, 50, and 100 µg/ml) of oleandrin or a *N. oleander* extract for 72 hrs as described herein. As a negative control, the cells were also treated with increasing amounts (1.5, 7.5, and 15 µl) of the vehicle solution which corresponded to the volumes used in the drug-treated cultures. Cyclophosphamide (50 µM; Sigma-Aldrich)-treated cells were included as a positive control for apoptosis. Then, the samples were washed and stained with Annexin V-FITC and propidium iodide (PI) and analyzed by confocal fluorescence-microscopy. The relative percentages of Annexin V-FITC and/or PI-positive cells were quantified by fluorescence-microscopy and counting triplicate visual fields using a 20× objective lens.

The results (FIG. 15 and FIGS. 16A-16F) indicate that the lowest concentration (10 µg/ml) of oleandrin and the *N. oleander* extract did not induce significant cytotoxicity/apoptosis. However, the higher concentrations (about 50 and about 100 µg/ml) of the crude phytoextract induced notably more apoptosis than did the oleandrin compound. This is consistent with the fact that oleandrin represents about 1.23% of the *N. oleander* extract. The cytotoxicity caused by oleandrin was not significantly higher than the Vehicle control in treated HTLV-1+ SLB1 cells.

We then investigated whether oleandrin or a *N. oleander* extract could inhibit virus transmission from a Green Fluorescent Protein (GFP)-expressing HTLV-1+ lymphoma T-cell-line to huPBMCs in co-culture assays (Example 20). For these studies, HTLV-1+ SLB1 lymphoma T-cells were treated with increasing concentrations of either the oleandrin compound or *N. oleander* extract, or the Vehicle control for 72 hrs in 96-well microtiter plates, and then the virus-containing supernatants were collected and used to directly infect primary cultured, human peripheral blood mononuclear cells (huPBMCs) in vitro. Following 72 hrs, the relative levels of extracellular $p19^{Gag}$-containing virus particles released into the culture supernatants, as a result of direct infection, were quantified by performing Anti-HTLV-1 $p19^{Gag}$ ELISAs.

The HTLV-1+ SLB1 lymphoma T-cell-line was treated with the Vehicle control, or increasing concentrations (10 µg/ml, 50 µg/ml, and 100 µg/ml) of the *N. oleander* extract or oleandrin compound for 72 hrs and then the virus-containing supernatants were collected and used to directly infect primary huPBMCs. The vehicle control, *N. oleander* extract, or oleandrin were also included in the culture media for the huPBMCs. After 72 hrs, the culture supernatants were collected and the relative amounts of extracellular virus particles produced were quantified by performing Anti-HTLV-1 $p19^{Gag}$ ELISAs.

The data (FIG. 17) indicate that the even lowest concentration (10 µg/ml) of both oleandrin and the *N. oleander* extract inhibited the infectivity of newly-synthesized $p19^{Gag}$-containing virus particles released into the culture supernatants of treated cells, relative to a comparable amount of the vehicle control. Both oleandrin and the crude phytoextract inhibited the formation of virological synapses and the transmission of HTLV-1 in vitro. Extracellular virus particles produced by oleandrin-treated HTLV-1+ lymphoma T-cells exhibit reduced infectivity on primary huPBMCs. Importantly, oleandrin exhibits antiviral activity against enveloped viruses by reducing the incorporation of the envelope glycoprotein into mature particles, which represents a unique stage of the retroviral infection cycle.

To ensure that the antiviral activity observed was not an artifact due to potential cytotoxicity of the antiviral composition to treated huPBMCs, we also investigated (Example 21) the cytotoxicity of purified oleandrin and the *N. oleander* extract, compared to the vehicle negative control, in treated huPBMCs. Primary buffy-coat huPBMCs were isolated and stimulated with phytohemagglutinin (PHA) and cultured in the presence of recombinant human interleukin-2 (hIL-2). The cells were then treated for 72 hrs with increasing concentrations of oleandrin or a *N. oleander* extract, or with increasing volumes of the Vehicle. The samples were subsequently stained with Annexin V-FITC and PI and the relative percentages of apoptotic (i.e., Annexin V-FITC and/or PI-positive) cells per field were quantified by confocal fluorescence-microscopy and counting in-triplicate.

Cytotoxic effects of the Vehicle control, *N. oleander* extract, and the oleandrin compound were assessed by treating primary huPBMCs for 72 hrs, and then the cultures were stained with Annexin V-FITC and PI. The relative percentages of apoptotic (i.e., Annexin V-FITC and/or PI-positive) cells were quantified by fluorescence-microscopy and counting triplicate visual fields using a 20× objective lens. The total numbers of cells were determined using DIC phase-contrast microscopy. Cyclophosphamide (50 µM)-treated cells were included as a positive control for apoptosis. NA indicates the number of cells in this sample was too low for accurate assessment due to higher toxicity.

The data (FIG. 18) indicate oleandrin exhibited moderate cytotoxicity (e.g., 35-37% at the lowest concentration) in huPBMCs as compared to the vehicle control. By contrast, the N. oleander extract was significantly cytotoxic and induced high levels of programmed cell-death even at the lowest concentration. The huPBMCs were somewhat more sensitive to purified oleandrin than the HTLV-1+ SLB1 lymphoblasts; however, the huPBMCs were drastically more sensitive to the crude N. oleander extract which also contains other cytotoxic compounds such as the triterpenes described herein.

We also investigated (Example 22) whether oleandrin or the N. oleander extract could interfere with the transmission of HTLV-1 particles to target huPBMCs in co-culture experiments. For these studies, the virus-producing HTLV-1+ SLB1 T-cell-line was treated with mitomycin C and then with increasing amounts of oleandrin, N. oleander extract, or the Vehicle control for either 15 min or 3 hrs. The SLB1 cells were washed 2× with serum-free medium and equivalent numbers of huPBMCs were then added to each well, and the samples were co-cultured for 72 hrs in complete medium at 37° C. under 10% $CO_2$ in a humidified incubator. The relative intercellular transmission of HTLV-1 was assessed by performing Anti-HTLV-1 $p19^{Gag}$ ELISAs to measure the levels of extracellular virus released into the culture supernatants.

Primary huPBMCs were co-cultured with mitomycin C-treated HTLV-1+ SLB1 lymphoma T-cells which were pre-treated for either 15 min or 3 hrs with the Vehicle control, or increasing concentrations (10 µg/ml, 50 µg/ml, and 100 µg/ml) of the N. oleander extract or oleandrin compound. The vehicle control, extract, and compound were also present in the co-culture media. After 72 hrs, the supernatants were collected, and the amounts of extracellular virus particles released were quantified by performing Anti-HTLV-1 $p19^{Gag}$ ELISAs.

Figure 19:
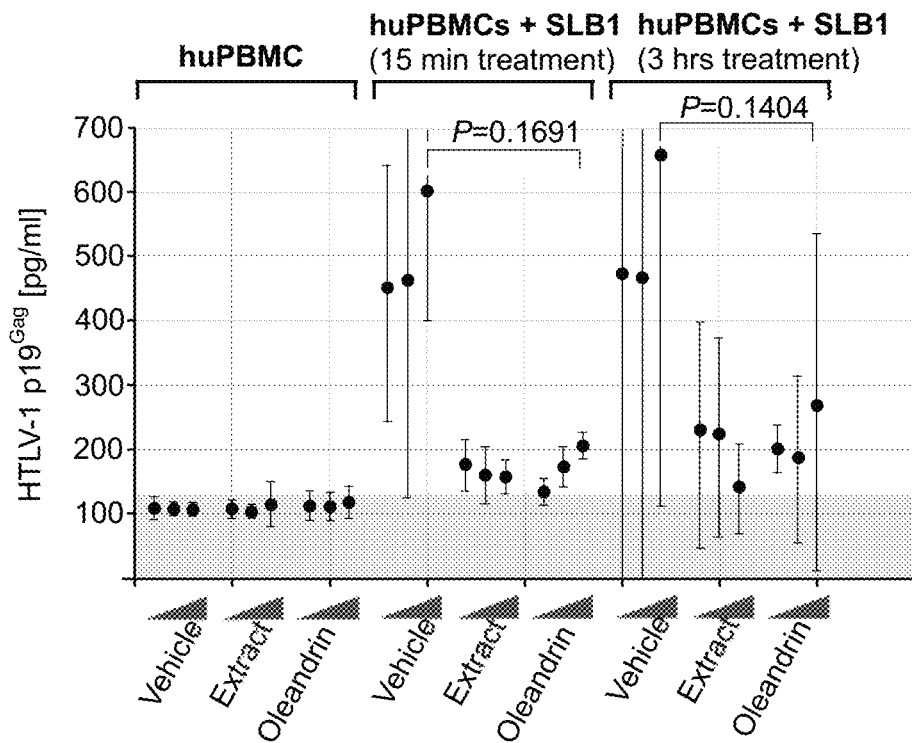
Figure 20:
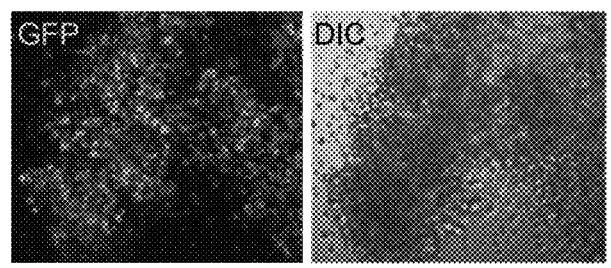
Figure 20:
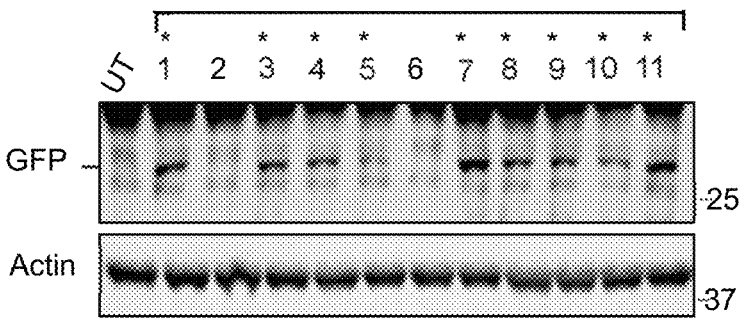

The results depicted in FIG. 19 demonstrate that both oleandrin and the N. oleander extract inhibited the transmission of HTLV-1 as compared to the vehicle control; although, there were no differences observed between the 15 min and 3 hrs of pre-treatment of the HTLV-1+ SLB1 cells We also investigated whether oleandrin inhibits virological synapse-formation and the transmission of HTLV-1 in co-culture assays (Example 22). A GFP-expressing HTLV-1+ SLB1 T-cell-line was generated by transducing SLB1 lymphoma T-cells with a pLenti-6.2/VS-DEST-GFP vector with selection on blasticidin (5 µg/ml; Life Technologies) for two weeks. The GFP-positive clones were screened by fluorescence-microscopy (FIG. 20 top panels) and immunoblotting (FIG. 20 lower panels) and expanded and repeatedly passaged. The DIC phase-contrast image is provided for comparison.

Figure 21:
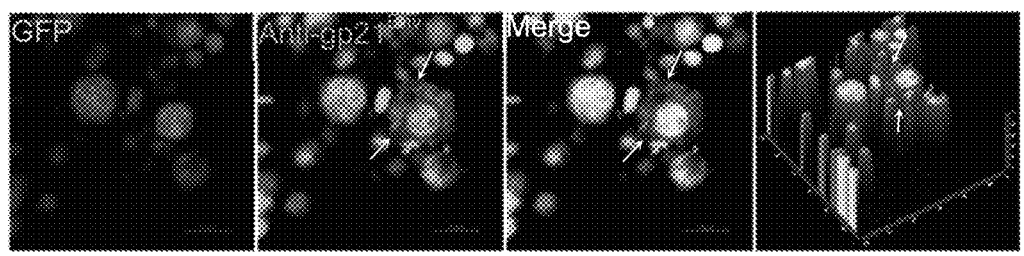
Figure 21:
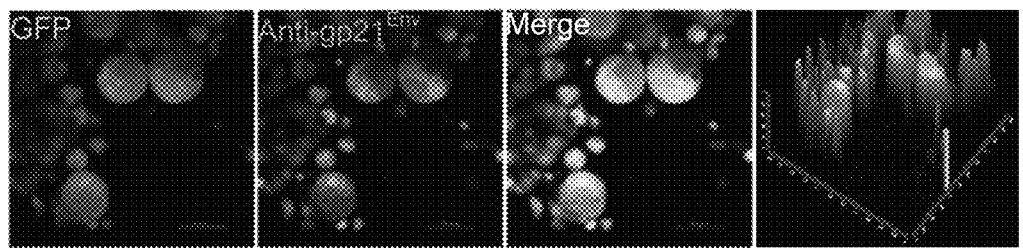
Figure 21:
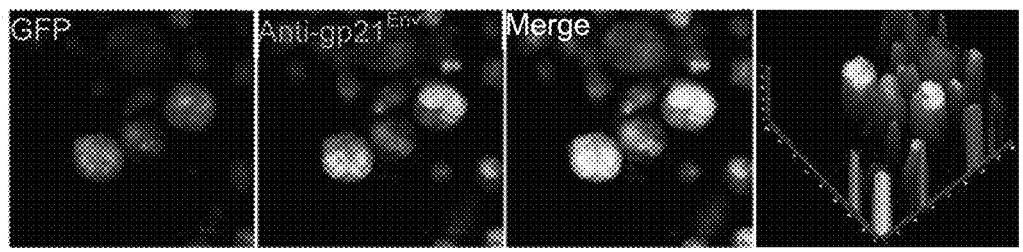
Figure 22:
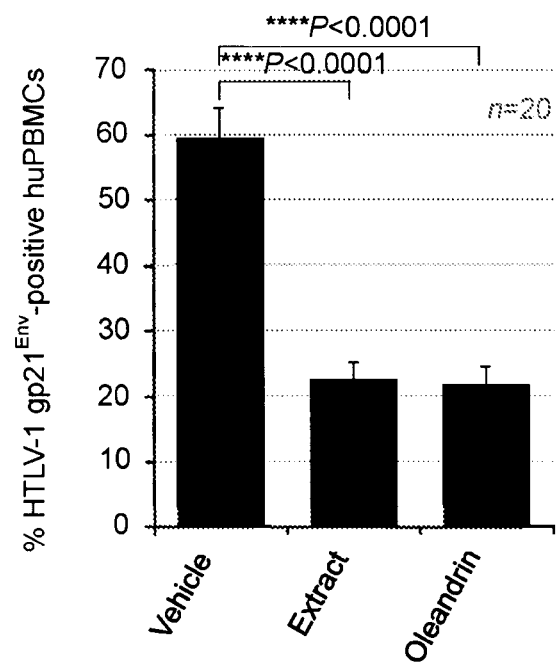

The formation of virological synapses between huPBMCs and the mitomycin C-treated HTLV-1+ SLB1/pLenti-GFP lymphoblasts (green cells) that had been pre-treated for 3 hrs with the Vehicle control or increasing amounts (10 µg/ml, 50 µg/ml, and 100 µg/ml) of the N. oleander extract or oleandrin compound were visualized by fluorescence-microscopy (FIG. 21). Virus transmission was assessed by quantifying the relative percentages of infected (i.e., HTLV-1 gp21-positive, red) huPBMCs (GFP-negative) in 20 visual fields (n=20) by fluorescence-microscopy using a 20× objective lens (see arrows in the Vehicle control panels). The fluorescence-microscopy data was quantified (FIG. 22). The data confirm that the antiviral composition inhibits virological synapse-formation and the transmission of HTLV-1 in co-culture assays.

The invention, thus, also provides a method of inhibiting (reducing) the infectivity of HTLV-1 particles released into the culture supernatants of treated cells and also reducing the intercellular transmission of HTLV-1 by inhibiting the Env-dependent formation of virological synapses, the method comprising treating virus-infected cells (in vitro or in vivo) with an effective amount of the antiviral composition.

Antiviral activity of the compositions herein was evaluated against rhinovirus infection. Rhinovirus is of the Picornaviridae family and Enterovirus genus. It is not enveloped and is an ss-RNA virus of (+) polarity. Oleandrin was found to be inactive against rhinovirus in the concentrations and assays employed herein, because it did not inhibit viral replication.

PBI-05204 (as described herein and in U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference) comprises cardiac glycoside (oleandrin, OL) and triterpenes (oleanolic acid (OA), ursolic acid (UA) and betulinic acid (BA)) as the primary pharmacologically active components. The molar ratio of OL to total triterpene is about 1:(10-96). The molar ratio of OA:UA:BA is about 7.8:7.4:1. The combination of OA, UA and BA in PBI-05204 increases the antiviral activity of oleandrin when compared on an OL equimolar basis. PBI-04711 is a fraction of PBI-05204, but it does not contain cardiac glycoside (OL). The molar ratio of OA:UA:BA in PBI-04711 is about 3:2.2:1. PBI-04711 also possesses antiviral activity. Accordingly, an antiviral composition comprising OL, OA, UA, and BA is more efficacious than a composition comprising OL as the sole active ingredient based upon an equimolar content of OL. In some embodiments, the molar ratios of the individual triterpenes to oleandrin range as follows: about 2-8 (OA):about 2-8 (UA):about 0.1-1 (BA):about 0.5-1.5 (OL); or about 3-6 (OA):about 3-6 (UA):about 0.3-8 (BA):about 0.7-1.2 (OL); or about 4-5 (OA):about 4-5 (UA):about 0.4-0.7 (BA):about 0.9-1.1 (OL); or about 4.6 (OA):about 4.4 (UA):about 0.6 (BA):about 1 (OL).

Antiviral compositions comprising oleandrin as the sole antiviral agent are within the scope of the invention.

Antiviral compositions comprising oleandrin and plural triterpenes as the antiviral agents are within the scope of the invention. In some embodiments, the antiviral composition comprises oleandrin, oleanolic acid (free acid, salt, derivative or prodrug thereof), ursolic acid (free acid, salt, derivative or prodrug thereof), and betulinic acid (free acid, salt, derivative or prodrug thereof). The molar ratios of the compounds is as described herein.

Antiviral compositions comprising plural triterpenes as the primary active ingredients (meaning excluding steroid, cardiac glycoside and pharmacologically active components) are also within the scope of the invention. As noted above, PBI-04711 comprises OA, UA and BA as the primary active ingredients, and it exhibits antiviral activity. In some embodiments, a triterpene-based antiviral composition comprises OA, UA and BA, each of which is independently selected upon each occurrence from its free acid form, salt form, deuterated form and derivative form.

PBI-01011 is an improved triterpene-based antiviral composition comprising OA, UA and BA, wherein the molar ratio of OA:UA:BA is about 9-12: up to about 2: up to about 2, or about 10:about 1:about 1, or about 9-12:about 0.1-2: about 0.1-2, or about 9-11:about 0.5-1.5:about 0.5-1.5, or about 9.5-10.5:about 0.75-1.25:about 0.75-1.25, or about 9.5-10.5:about 0.8-1.2:about 0.8-1.2, or about 9.75-10.5: about 0.9-1.1:about 0.9-1.1.

In some embodiments, an antiviral composition comprises at least oleanolic acid (free acid, salt, derivative or prodrug thereof) and ursolic acid (free acid, salt, derivative or prodrug thereof) present at a molar ratio of OA to UA as described herein. OA is present in large molar excess over UA.

In some embodiments, an antiviral composition comprises at least oleanolic acid (free acid, salt, derivative or prodrug thereof) and betulinic acid (free acid, salt, derivative or prodrug thereof) present at a molar ratio of OA to BA as described herein. OA is present in large molar excess over BA.

In some embodiments, an antiviral composition comprises at least oleanolic acid (free acid, salt, derivative or prodrug thereof), ursolic acid (free acid, salt, derivative or prodrug thereof), and betulinic acid (free acid, salt, derivative or prodrug thereof) present at a molar ratio of OA to UA to BA as described herein. OA is present in large molar excess over both UA and BA.

In some embodiments, a triterpene-based antiviral composition excludes cardiac glycoside.

In general, a subject having Filoviridae infection, Flaviviridae infection (*Flavivirus* genus), *Deltaretrovirus* genus, or Togaviridae infection is treated as follows. The subject is evaluated to determine whether said subject is infected with said virus. Administration of antiviral composition is indicated. Initial doses of antiviral composition are administered to the subject according to a prescribed dosing regimen for a period of time (a treatment period). The subject's clinical response and level of therapeutic response are determined periodically. If the level of therapeutic response is too low at one dose, then the dose is escalated according to a predetermine dose escalation schedule until the desired level of therapeutic response in the subject is achieved. Treatment of the subject with antiviral composition is continued as needed. The dose or dosing regimen can be adjusted as needed until the patient reaches the desired clinical endpoint(s) such as cessation of the infection itself, reduction in infection-associated symptoms, and/or a reduction in the progression of the infection.

If a clinician intends to treat a subject having viral infection with a combination of a antiviral composition and one or more other therapeutic agents, and it is known that the viral infection, which the subject has, is at least partially therapeutically responsive to treatment with said one or more other therapeutic agents, then the present method invention comprises: administering to the subject in need thereof a therapeutically relevant dose of antiviral composition and a therapeutically relevant dose of said one or more other therapeutic agents, wherein the antiviral composition is administered according to a first dosing regimen and the one or more other therapeutic agents is administered according to a second dosing regimen. In some embodiments, the first and second dosing regimens are the same. In some embodiments, the first and second dosing regimens are different.

The antiviral composition(s) of the invention can be administered as primary antiviral therapy, adjunct antiviral therapy, or co-antiviral therapy. Methods of the invention include separate administration or coadministration of the antiviral composition with at least one other known antiviral composition, meaning the antiviral composition of the invention can be administered before, during or after administration of a known antiviral composition (compound(s)) or of a composition for treating symptoms associated with the viral infection. For example, medications used to treat inflammation, vomiting, nausea, headache, fever, diarrhea, nausea, hives, conjunctivitis, malaise, muscle pain, joint pain, seizure, or paralysis can be administered with or separately from the antiviral composition of the invention.

The one or more other therapeutic agents can be administered at doses and according to dosing regimens that are clinician-recognized as being therapeutically effective or at doses that are clinician-recognized as being sub-therapeutically effective. The clinical benefit and/or therapeutic effect provided by administration of a combination of antiviral composition and one or more other therapeutic can be additive or synergistic, such level of benefit or effect being determined by comparison of administration of the combination to administration of the individual antiviral composition component(s) and one or more other therapeutic agents. The one or more other therapeutic agents can be administered at doses and according to dosing regimens as suggested or described by the Food and Drug Administration, World Health Organization, European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

Exemplary other therapeutic agents that can be included in the antiviral composition of the invention for the treatment of HTLV-1 virus infection include antiretroviral agent, interferon alpha (IFN-a), zidovudine, lamivudine, cyclosporine A, CHOP with arsenic trioxide, sodium valproate, methotrexate, azathioprine, one or more symptom alleviating drug(s), steroid sparing drug, corticosteroid, cyclophosphamide, and combinations thereof. Therapies studied include plasmapheresis and radiation.

Example 5 provides an exemplary procedure for the treatment of Zikavirus infection in a mammal. Example 12 provides an exemplary procedure for the treatment of Filovirus infection (Ebolavirus, Marburgvirus) in a mammal. Example 13 provides an exemplary procedure for the treatment of *Flavivirus* infection (Yellow Fever, Dengue Fever, Japanese Enchephalitis, West Nile Viruses, Zikavirus, Tickborne Encephalitis, Kyasanur Forest Disease, Alkhurma Disease, Omsk Hemorrhagic Fever, Powassan virus infection) in a mammal. Example 25 provides an exemplary procedure for the treatment of *Deltaretrovirus* genus (HTLV-1) infection.

The antiviral compound(s) (triterpene(s), cardiac glycoside(s), etc.) present in the pharmaceutical composition can be present in their unmodified form, salt form, derivative form or a combination thereof. As used herein, the term "derivative" is taken to mean: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosilated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

As used herein, the term "oleandrin" is taken to mean all known forms of oleandrin unless otherwise specified. Oleandrin can be present in racemic, optically pure or optically enriched form. *Nerium oleander* plant material can be obtained, for example, from commercial plant suppliers such as Aldridge Nursery, Atascosa, Tex.

The supercritical fluid (SCF) extract can be prepared as detailed in U.S. Pat. Nos. 7,402,325, 8,394,434, 8,187,644, or PCT International Publication No. WP 2007/016176 A2, the entire disclosures of which are hereby incorporated by reference. Extraction can be conducted with supercritical carbon dioxide in the presence or absence of a modifier (organic solvent) such as ethanol.

Other extracts containing cardiac glycoside, especially oleandrin, can be prepared by various different processes. An extract can be prepared according to the process developed by Dr. Huseyin Ziya Ozel (U.S. Pat. No. 5,135,745) describes a procedure for the preparation of a hot water extract. The aqueous extract reportedly contains several polysaccharides with molecular weights varying from 2 KD to 30 KD, oleandrin and oleandrigenin, odoroside and neritaloside. The polysaccharides reportedly include acidic homopolygalacturonans or arabinogalaturonans. U.S. Pat. No. 5,869,060 to Selvaraj et al. discloses hot water extracts of *Nerium* species and methods of production thereof, e.g. Example 2. The resultant extract can then be lyophilized to produce a powder. U.S. Pat. No. 6,565,897 (U.S. Pregnant Publication No. 20020114852 and PCT International Publication No. WO 2000/016793 to Selvaraj et al.) discloses a hot-water extraction process for the preparation of a substantially sterile extract. Erdemoglu et al. (*J. Ethnopharmacol.* (2003) November 89(1), 123-129) discloses results for the comparison of aqueous and ethanolic extracts of plants, including *Nerium oleander*, based upon their anti-nociceptive and anti-inflammatory activities. Organic solvent extracts of *Nerium oleander* are disclosed by Adome et al. (*Afr. Health Sci.* (2003) August 3(2), 77-86; ethanolic extract), el-Shazly et al. (*J. Egypt Soc. Parasitol.* (1996), August 26(2), 461-473; ethanolic extract), Begum et al. (*Phytochemistry* (1999) February 50(3), 435-438; methanolic extract), Zia et al. (*J. Ethnolpharmacol.* (1995) November 49(1), 33-39; methanolic extract), and Vlasenko et al. (*Farmatsiia.* (1972) September-October 21(5), 46-47; alcoholic extract). U.S. Pregnant Patent Application Publication No. 20040247660 to Singh et al. discloses the preparation of a protein stabilized liposomal formulation of oleandrin for use in the treatment of cancer. U.S. Pregnant Patent Application Publication No. 20050026849 to Singh et al. discloses a water soluble formulation of oleandrin containing a cyclodextrin. U.S. Pregnant Patent Application Publication No. 20040082521 to Singh et al. discloses the preparation of protein stabilized nanoparticle formulations of oleandrin from the hot-water extract.

The extracts also differ in their polysaccharide and carbohydrate content. The hot water extract contains 407.3 glucose equivalent units of carbohydrate relative to a standard curve prepared with glucose while analysis of the SCF $CO_2$ extract found carbohydrate levels that were found in very low levels that were below the limit of quantitation. The amount of carbohydrate in the hot water extract of *Nerium oleander* was, however, at least 100-fold greater than that in the SCF $CO_2$ extract. The polysaccharide content of the SCF extract can be 0%, <0.5%, <0.1%, <0.05%, or <0.01% wt. In some embodiments, the SCF extract excludes polysaccharide obtained during extraction of the plant mass.

| *Nerium oleander* preparation | Carbohydrate content (μg glucose equivalents/mg of plant extract) |
|---|---|
| Hot water extract | 407.3 ± 6.3 |
| SCF $CO_2$ extract | BLQ (below limit of quantitation) |

The partial compositions of the SCF $CO_2$ extract and hot water extract were determined by DART TOF-MS (Direct Analysis in Real Time Time of Flight Mass Spectrometry) on a JEOL AccuTOF-DART mass spectrometer (JEOL USA, Peabody, Mass., USA).

The SCF extract of *Nerium* species or *Thevetia* species is a mixture of pharmacologically active compounds, such as oleandrin and triterpenes. The extract obtained by the SCF process is a substantially water-insoluble, viscous semi-solid (after solvent is removed) at ambient temperature. The SCF extract comprises many different components possessing a variety of different ranges of water solubility. The extract from a supercritical fluid process contains by weight a theoretical range of 0.9% to 2.5% wt of oleandrin or 1.7% to 2.1% wt of oleandrin or 1.7% to 2.0% wt of oleandrin. SCF extracts comprising varying amount of oleandrin have been obtained. In one embodiment, the SCF extract comprises about 2% by wt. of oleandrin. The SCF extract contains a 3-10 fold higher concentration of oleandrin than the hot-water extract. This was confirmed by both HPLC as well as LC/MS/MS (tandem mass spectrometry) analyses.

The SCF extract comprises oleandrin and the triterpenes oleanolic acid, betulinic acid and ursolic acid and optionally other components as described herein. The content of oleandrin and the triterpenes can vary from batch to batch; however, the degree of variation is not excessive. For example, a batch of SCF extract (PBI-05204) was analyzed for these four components and found to contain the following approximate amounts of each.

|  | Oleandrin | Oleanolic acid | Ursolic acid | Betulinic acid |
|---|---|---|---|---|
| Content of component (mg/g of SCF extract) | 20 | 73 | 69 | 9.4 |
| Content of component (% wt WRT g of SCT extract) | 2 | 7.3 | 6.9 | 0.94 |
| Content of component (mmole/g of SCF extract) | 34.7 | 160 | 152 | 20.6 |
| Molar ratio of component WRT oleandrin | 1 | 4.6 | 4.4 | 0.6 |

WRT denotes "with respect to".

The content of the individual components may vary by ±25%, ±20%, ±15%, ±10% or ±5% relative to the values indicated. Accordingly, the content of oleandrin in the SCF extract would be in the range of 20 mg±5 mg (which is ±25% of 20 mg) per mg of SCF extract.

Oleandrin, oleanolic acid, ursolic acid, betulinic acid and derivatives thereof can also be purchased from Sigma-Aldrich (www.sigmaaldrich.com; St. Louis, Mo., USA).

As used herein, the individually named triterpenes can independently be selected upon each occurrence in their native (unmodified, free acid) form, in their salt form, in derivative form, prodrug form, or a combination thereof. Compositions containing and methods employing deuterated forms of the triterpenes are also within the scope of the invention.

Oleanolic acid derivatives, prodrugs and salts are disclosed in US 20150011627 A1 to Gribble et al. which published Jan. 8, 2015, US 20140343108 A1 to Rong et al which published Nov. 20, 2014, US 20140343064 A1 to Xu et al. which published Nov. 20, 2014, US 20140179928 A1 to Anderson et al. which published Jun. 26, 2014, US 20140100227 A1 to Bender et al. which published Apr. 10, 2014, US 20140088188 A1 to Jiang et al. which published Mar. 27, 2014, US 20140088163 A1 to Jiang et al. which published Mar. 27, 2014, US 20140066408 A1 to Jiang et al. which published Mar. 6, 2014, US 20130317007 A1 to Anderson et al. which published Nov. 28, 2013, US 20130303607 A1 to Gribble et al. which published Nov. 14, 2013, US 20120245374 to Anderson et al. which published Sep. 27, 2012, US 20120238767 A1 to Jiang et al. which published Sep. 20, 2012, US 20120237629 A1 to Shode et al. which published Sep. 20, 2012, US 20120214814 A1 to Anderson et al. which published Aug. 23, 2012, US 20120165279 A1 to Lee et al. which published Jun. 28, 2012, US 20110294752 A1 to Arntzen et al. which published Dec. 1, 2011, US 20110091398 A1 to Majeed et al. which published Apr. 21, 2011, US 20100189824 A1 to Arntzen et al. which published Jul. 29, 2010, US 20100048911 A1 to Jiang et al. which published Feb. 25, 2010, and US 20060073222 A1 to Arntzen et al. which published Apr. 6, 2006, the entire disclosures of which are hereby incorporated by reference.

Ursolic acid derivatives, prodrugs and salts are disclosed in US 20150011627 A1 to Gribble et al. which published Jan. 8, 2015, US 20130303607 A1 to Gribble et al. which published Nov. 14, 2013, US 20150218206 A1 to Yoon et al. which published Aug. 6, 2015, U.S. Pat. No. 6,824,811 to Fritsche et al. which issued Nov. 30, 2004, U.S. Pat. No. 7,718,635 to Ochiai et al. which issued May 8, 2010, U.S. Pat. No. 8,729,055 to Lin et al. which issued May 20, 2014, and U.S. Pat. No. 9,120,839 to Yoon et al. which issued Sep. 1, 2015, the entire disclosures of which are hereby incorporated by reference.

Betulinic acid derivatives, prodrugs and salts are disclosed in US 20150011627 A1 to Gribble et al. which published Jan. 8, 2015, US 20130303607 A1 to Gribble et al. which published Nov. 14, 2013, US 20120237629 A1 to Shode et al. which published Sep. 20, 2012, US 20170204133 A1 to Regueiro-Ren et al. which published Jul. 20, 2017, US 20170096446 A1 to Nitz et al. which published Apr. 6, 2017, US 20150337004 A1 to Parthasaradhi Reddy et al. which published Nov. 26, 2015, US 20150119373 A1 to Parthasaradhi Reddy et al. which published Apr. 30, 2015, US 20140296546 A1 to Yan et al. which published Oct. 2, 2014, US 20140243298 A1 to Swidorski et al. which published Aug. 28, 2014, US 20140221328 A1 to Parthasaradhi Reddy et al. which published Aug. 7, 2014, US 20140066416 A1 tp Leunis et al. which published Mar. 6, 2014, US 20130065868 A1 to Durst et al. which published Mar. 14, 2013, US 20130029954 A1 to Regueiro-Ren et al. which published Jan. 31, 2013, US 20120302530 A1 to Zhang et al. which published Nov. 29, 2012, US 20120214775 A1 to Power et al. which published Aug. 23, 2012, US 20120101149 A1 to Honda et al. which published Apr. 26, 2012, US 20110224182 to Bullock et al. which published Sep. 15, 2011, US 20110313191 A1 to Hemp et al. which published Dec. 22, 2011, US 20110224159 A1 to Pichette et al. which published Sep. 15, 2011, US 20110218204 to Parthasaradhi Reddy et al. which published Sep. 8, 2011, US 20090203661 A1 to Safe et al. which published Aug. 13, 2009, US 20090131714 A1 to Krasutsky et al. which published May 21, 2009, US 20090076290 to Krasutsky et al. which published Mar. 19, 2009, US 20090068257 A1 to Leunis et al. which published Mar. 12, 2009, US 20080293682 to Mukherjee et al. which published Nov. 27, 2008, US 20070072835 A1 to Pezzuto et al. which published Mar. 29, 2007, US 20060252733 A1 to Jansen et al. which published Nov. 9, 2006, and US 2006025274 A1 to O'Neill et al. which published Nov. 9, 2006, the entire disclosures of which are hereby incorporated by reference.

The antiviral composition can be formulated in any suitable pharmaceutically acceptable dosage form. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

Suitable dosage forms containing the antiviral composition can be prepared by mixing the antiviral composition with pharmaceutically acceptable excipients as described herein or as described in Pi et al. ("Ursolic acid nanocrystals for dissolution rate and bioavailability enhancement: influence of different particle size" in Curr. Drug Deliv. (March 2016), 13(8), 1358-1366), Yang et al. ("Self-microemulsifying drug delivery system for improved oral bioavailability of oleanolic acid: design and evaluation" in Int. J. Nanomed. (2013), 8(1), 2917-2926), Li et al. (Development and evaluation of optimized sucrose ester stabilized oleanolic acid nanosuspensions prepared by wet ball milling with design of experiments" in Biol. Pharm. Bull. (2014), 37(6), 926-937), Zhang et al. ("Enhancement of oral bioavailability of triterpene through lipid nanospheres: preparation, characterization, and absorption evaluation" in J. Pharm. Sci. (June 2014), 103(6), 1711-1719), Godugu et al. ("Approaches to improve the oral bioavailability and effects of novel anticancer drugs berberine and betulinic acid" in PLoS One (March 2014), 9(3):e89919), Zhao et al. ("Preparation and characterization of betulin nanoparticles for oral hypoglycemic drug by antisolvent precipitation" in Drug Deliv. (September 2014), 21(6), 467-479), Yang et al. ("Physicochemical properties and oral bioavailability of ursolic acid nanoparticles using supercritical anti-solvent (SAS) process" in Food Chem. (May 2012), 132(1), 319-325), Cao et al. ("Ethylene glycol-linked amino acid diester prodrugs of oleanolic acid for PEPT1-mediated transport: synthesis, intestinal permeability and pharmacokinetics" in Mol. Pharm. (August 2012), 9(8), 2127-2135), Li et al. ("Formulation, biological and pharmacokinetic studies of sucrose ester-stabilized nanosuspensions of oleanolic acid" in Pharm. Res. (August 2011), 28(8), 2020-2033), Tong et al. ("Spray freeze drying with polyvinylpyrrolidone and sodium caprate for improved dissolution and oral bioavailablity of oleanolic acid, a BCS Class IV compound" in Int. J. Pharm. (February 2011), 404(1-2), 148-158), Xi et al. (Formulation development and bioavailability evaluation of a self-nanoemulsified drug delivery system of oleanolic acid" in AAPS PharmSciTech (2009), 10(1), 172-182), Chen et al. ("Oleanolic acid nanosuspensions: preparation, in-vitro characterization and enhanced hepatoprotective effect" in J. Pharm. Pharmacol. (February 2005), 57(2), 259-264), the entire disclosures of which are hereby incorporated by reference.

Suitable dosage forms can also be made according to U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference. Suitable dosage forms can also be made as described in Examples 13-15.

An effective amount or therapeutically relevant amount of antiviral compound (cardiac glycoside, triterpene or combinations thereof) is specifically contemplated. By the term "effective amount", it is understood that a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response may occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The desired dose for oral administration is up to 5 dosage forms although as few as one and as many as ten dosage forms may be administered as a single dose. Exemplary dosage forms can contain 0.01-100 mg or 0.01-100 microg of the antiviral composition per dosage form, for a total 0.1 to 500 mg (1 to 10 dose levels) per dose. Doses will be administered according to dosing regimens that may be predetermined and/or tailored to achieve specific therapeutic response or clinical benefit in a subject.

The cardiac glycoside can be present in a dosage form in an amount sufficient to provide a subject with an initial dose of oleandrin of about 20 to about 100 microg, about 12 microg to about 300 microg, or about 12 microg to about 120 microg. A dosage form can comprise about 20 of oleandrin to about 100 microg, about 0.01 microg to about 100 mg or about 0.01 microg to about 100 microg oleandrin, oleandrin extract or extract of *Nerium oleander* containing oleandrin.

The antiviral can be included in an oral dosage form. Some embodiments of the dosage form are not enteric coated and release their charge of antiviral composition within a period of 0.5 to 1 hours or less. Some embodiments of the dosage form are enteric coated and release their charge of antiviral composition downstream of the stomach, such as from the jejunum, ileum, small intestine, and/or large intestine (colon). Enterically coated dosage forms will release antiviral composition into the systemic circulation within 1-10 hr after oral administration.

The antiviral composition can be included in a rapid release, immediate release, controlled release, sustained release, prolonged release, extended release, burst release, continuous release, slow release, or pulsed release dosage form or in a dosage form that exhibits two or more of those types of release. The release profile of antiviral composition from the dosage form can be a zero order, pseudo-zero, first order, pseudo-first order or sigmoidal release profile. The plasma concentration profile for triterpene in a subject to which the antiviral composition is administered can exhibit one or more maxima.

Based on human clinical data it is anticipated that 50% to 75% of an administered dose of oleandrin will be orally bioavailable therefore providing about 10 to about 20 microg, about 20 to about 40 microg, about 30 to about 50 microg, about 40 to about 60 microg, about 50 to about 75 microg, about 75 to about 100 microg of oleandrin per dosage form. Given an average blood volume in adult humans of 5 liters, the anticipated oleandrin plasma concentration will be in the range of about 0.05 to about 2 ng/ml, about 0.005 to about 10 ng/mL, about 0.005 to about 8 ng/mL, about 0.01 to about 7 ng/mL, about 0.02 to about 7 ng/mL, about 0.03 to about 6 ng/mL, about 0.04 to about 5 ng/mL, or about 0.05 to about 2.5 ng/mL. The recommended daily dose of oleandrin, present in the SCF extract, is generally about 0.2 microg to about 4.5 microg/kg body weight twice daily. The dose of oleandrin can be about 0.2 to about 1 microg/kg body weight/day, about 0.5 to about 1.0 microg/kg body weight/day, about 0.75 to about 1.5 microg/kg body weight/day, about 1.5 to about 2.52 microg/kg body weight/day, about 2.5 to about 3.0 microg/kg body weight/day, about 3.0 to 4.0 microg/kg body weight/day or about 3.5 to 4.5 microg oleandrin/kg body weight/day. The maximum tolerated dose of oleandrin can be about about 3.5 microg/kg body weight/day to about 4.0 microg/kg body weight/day. The minimum effective dose can be about 0.5 microg/day, about 1 microg/day, about 1.5 microg/day, about 1.8 microg/day, about 2 microg/day, or about 5 microg/day.

The antiviral composition can be administered at low to high dose due to the combination of triterpenes present and the molar ratio at which they are present. A therapeutically effective dose for humans is about 100-1000 mg or about 100-1000 microg of antiviral composition per Kg of body weight. Such a dose can be administered up to 10 times in a 24-hour period. Other suitable dosing ranges are specified below.

| Composition | Oleandrin (moles) | Oleanolic acid (moles) | Ursolic acid (moles) | Betulinic acid (moles) | Suitable dose |
|---|---|---|---|---|---|
| A | 0.5-1.5 | 4-6 | — | — | 0.05 to 0.5 mg/kg/day |
| B | 0.5-1.5 | 4-6 | 4-6 | — | 0.05 to 0.35 mg/kg/day |
| C (PBI-05204) | 0.5-1.5 | 4-6 | 4-6 | 0.1-1 | 0.05 to 0.22 mg/kg/day |
| D | 0.5-1.5 | — | 4-6 | — | 0.05 to 0.4 mg/kg/day |
| E | 0.5-1.5 | — | — | 0.1-1 | 0.05 to 0.4 mg/kg/day |
| AA | About 1 | — | — | 0.3-0.7 | 0.05 to 0.4 mg/kg/day |
| AB | About 1 | About 4.7 | — | — | 0.05 to 0.5 mg/kg/day |
| AC | About 1 | About 4.7 | About 4.5 | — | 0.05 to 0.4 mg/kg/day |

-continued

| Composition | Oleandrin (moles) | Oleanolic acid (moles) | Ursolic acid (moles) | Betulinic acid (moles) | Suitable dose |
|---|---|---|---|---|---|
| AD (PBI-05204) | About 1 | About 4.7 | About 4.5 | About 0.6 | 0.05 to 0.22 mg/kg/day |
| AE | About 1 | — | About 4.5 | — | 0.05 to 0.4 mg/kg/day |
| AF | About 1 | — | — | About 0.6 | 0.05 to 0.3 mg/kg/day |

All values are approximate, meaning "about" the specified value.

It should be noted that a compound herein might possess one or more functions in a composition or formulation of the invention. For example, a compound might serve as both a surfactant and a water miscible solvent or as both a surfactant and a water immiscible solvent.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Exemplary solvents are listed as class 2 or class 3 solvents. Class 3 solvents include, for example, acetic acid, acetone, anisole, 1-butanol, 2-butanol, butyl acetate, tert-butylmethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethythexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G10O: Decaglycerol Decaoleate; Caprol 3GO: Triglycerol Monooleate; Caprol ET: Polyglycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinylpyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

Although not necessary, the composition or formulation may further comprise one or more chelating agents, one or more preservatives, one or more antioxidants, one or more adsorbents, one or more acidifying agents, one or more alkalizing agents, one or more antifoaming agents, one or more buffering agents, one or more colorants, one or more electrolytes, one or more salts, one or more stabilizers, one or more tonicity modifiers, one or more diluents, or a combination thereof.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly (ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base, free acid or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. On the other hand, where the pharmacologically active ingredient possesses an acid functional group, a pharmaceutically acceptable base is added to form the pharmaceutically acceptable salt. Lists of other suitable salts are found in *Remington's Pharmaceutical Sciences*, 17th. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

A dosage form can be made by any conventional means known in the pharmaceutical industry. A liquid dosage form can be prepared by providing at least one liquid carrier and antiviral composition in a container. One or more other excipients can be included in the liquid dosage form. A solid dosage form can be prepared by providing at least one solid carrier and antiviral composition. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container.

The composition of the invention can be included in any dosage form. Particular dosage forms include a solid or liquid dosage forms. Exemplary suitable dosage forms include tablet, capsule, pill, caplet, troche, sache, and other such dosage forms known to the artisan of ordinary skill in the pharmaceutical sciences.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Example 1

Supercritical Fluid Extraction of Powdered Oleander Leaves

Method A. With Carbon Dioxide.

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll and other residual chromophoric compounds. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. With Mixture of Carbon Dioxide and Ethanol

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 0.91%.

Example 2

Hot-Water Extraction of Powdered Oleander Leaves

Comparative Example

Hot water extraction is typically used to extract oleandrin and other active components from oleander leaves. Examples of hot water extraction processes can be found in U.S. Pat. Nos. 5,135,745 and 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%.

Example 3

Preparation of Pharmaceutical Compositions

Method A. Cremophor-Based Drug Delivery System

The following ingredients were provided in the amounts indicated.

| Reagent Name | Function | Percent of Formulation (% w/w) |
|---|---|---|
| Antiviral composition | Active agent | 3.7 |
| Vitamin E | Antioxidant | 0.1 |
| Labrasol | Surfactant | 9.2 |
| Ethanol | Co-solvent | 9.6 |
| Cremophor EL | Surfactant | 62.6 |
| Cremophor RH40 | Surfactant | 14.7 |

The excipients were dispensed into ajar and shook in a New Brunswick Scientific C24KC Refrigerated Incubator shaker for 24 hours at 60° C. to ensure homogeneity. The samples were then pulled and visually inspected for solubilization. Both the excipients and antiviral composition were totally dissolved for all formulations after 24 hours.

Method B. GMO/Cremophor-Based Drug Delivery System

The following ingredients were provided in the amounts indicated.

| Reagent Name | Function | Percent of Formulation (% w/w) |
|---|---|---|
| antiviral composition | Active agent | 4.7 |
| Vitamin E | Antioxidant | 0.1 |
| Labrasol | Surfactant | 8.5 |
| Ethanol | Co-solvent | 7.6 |
| Cremophor EL | Surfactant | 56.1 |
| Glycerol Monooleate | Surfactant | 23.2 |

The procedure of Method A was followed.

Method C. Labrasol-Based Drug Delivery System

The following ingredients were provided in the amounts indicated.

| Reagent Name | Function | Percent of Formulation (% w/w) |
|---|---|---|
| antiviral composition | Active agent | 3.7 |
| Vitamin E | Antioxidant | 0.1 |
| Labrasol | Surfactant | 86.6 |
| Ethanol | Co-solvent | 9.6 |

The procedure of Method A was followed.

Method D. Vitamin E-TPGS Based Micelle Forming System

The following ingredients were provided in the amounts indicated.

| Component | Function | Weight % (w/w) |
|---|---|---|
| Vitamin E | Antioxidant | 1.0 |
| Vitamin E TPGS | Surfactant | 95.2 |
| antiviral composition | Active agent | 3.8 |

The procedure of Method A was followed.

Method E. Multi-Component Drug Delivery System

The following ingredients were provided in the amounts indicated.

| Component | Weight (g) | Weight % (w/w) |
|---|---|---|
| Vitamin E | 10.0 | 1.0 |
| Cremophor ELP | 580.4 | 55.9 |
| Labrasol | 89.0 | 8.6 |
| Glycerol Monooleate | 241.0 | 23.2 |
| Ethanol | 80.0 | 7.7 |
| antiviral composition | 38.5 | 3.7 |
| Total | 1038.9 | 100 |

The procedure of Method A was followed.

Method F. Multi-Component Drug Delivery System

The following ingredients were provided in the amounts indicated an included in a capsule.

| Component | Tradename | Weight % (w/w) |
|---|---|---|
| antiviral composition | FLAVEX Naturextrakte | 0.6 |
| Vitamin E | | 1.3 |
| Caprylocaproyl polyoxyglycerides | Labrasol Gattefosse 3074TPD | 11.1 |
| Lauroyl polyoxyglycerides | Gelucire 44/14 Gattefosse 3061TPD | 14.6 |
| Polyoxyl 35 Castor oil | Kolliphor BASF Corp. 50251534 | 72.4 |
| Total | | 100 |

The procedure of Method A was followed.

Example 4

Preparation of Enteric Coated Capsules

Step I: Preparation of Liquid-Filled Capsule

Hard gelatin capsules (50 counts, 00 size) were filled with a liquid composition of Example 3. These capsules were manually filled with 800 mg of the formulation and then sealed by hand with a 50% ethanol/50% water solution. The capsules were then banded by hand with 22% gelatin solution containing the following ingredients in the amounts indicated.

| Ingredient | Wt. (g) |
|---|---|
| Gelatin | 140.0 |
| Polysorbate 80 | 6.0 |
| Water | 454.0 |
| Total | 650.0 |

The gelatin solution mixed thoroughly and allowed to swell for 1-2 hours. After the swelling period, the solution was covered tightly and placed in a 55° C. oven and allowed to liquefy. Once the entire gelatin solution was liquid, the banding was performed Using a pointed round 3/0 artist brush, the gelatin solution was painted onto the capsules. Banding kit provided by Shionogi was used. After the banding, the capsules were kept at ambient conditions for 12 hours to allow the band to cure.

Step II: Coating of Liquid-Filled Capsule

A coating dispersion was prepared from the ingredients listed in the table below.

| Ingredient | Wt. % | Solids % | Solids (g) | g/Batch |
|---|---|---|---|---|
| Eudragit L30D55 | 40.4 | 60.5 | 76.5 | 254.9 |
| TEC | 1.8 | 9.0 | 11.4 | 11.4 |
| AlTalc 500V | 6.1 | 30.5 | 38.5 | 38.5 |
| Water | 51.7 | na | na | 326.2 |
| Total | 100.0 | 100.0 | 126.4 | 631.0 |

If banded capsules according to Step I were used, the dispersion was applied to the capsules to a 20.0 mg/cm$^2$ coating level. The following conditions were used to coat the capsules.

| Parameters | Set-up |
|---|---|
| Coating Equipment | Vector LDCS-3 |
| Batch Size | 500 g |
| Inlet Air Temp. | 40° C. |
| Exhaust Air Temp. | 27-30° C. |
| Inlet Air Volume | 20-25 CFM |
| Pan Speed | 20 rpm |
| Pump Speed | 9 rpm (3.5 to 4.0 g/min) |
| Nozzle Pressure | 15 psi |
| Nozzle diameter | 1.0 mm |
| Distance from tablet bed* | 2-3 in |

*Spray nozzle was set such that both the nozzle and spray path were under the flow path of inlet air.

Example 5

Treatment of Zika Virus Infection in a Subject

Method A. Antiviral Composition Therapy

A subject presenting with Zika virus infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's Zika virus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.

Method B. Combination Therapy: Antiviral Composition with Another Agent

Method A, above, is followed except that the subject is prescribed and administered one or more other therapeutic agents for the treatment of Zika virus infection or symptoms thereof. Then one or more other therapeutic agents can be administered before, after or with the antiviral composition. Dose escalation (or de-escalation) of the one or more other therapeutic agents can also be done.

Example 6

In Vitro Evaluation of Antiviral Activity Against Zika Virus Infection

Method A. Pure Compound

Vero E6 cells (also known as Vero C1008 cells, ATTC No. CRL-1586; https://www.atcc.org/Products/All/CRL-1586.aspx) were infected with ZIKV (Zika virus strain PRVABC59; ATCC VR-1843; https://www.atcc.org/Products/All/VR-1843.aspx) at an MOI (multiplicity of infection) of 0.2 in the presence of cardiac glycoside. Cells were incubated with virus and compound for 1 hr, after which the inoculum and compound were discarded. Cells were given fresh medium and incubated for 48 hr, after which they were fixed with formalin and stained for ZIKV infection. Representative infection rates for oleandrin (FIG. 1A) and digoxin (FIG. 1B) as determined by scintigraphy are depicted. Other compounds are evaluated under the same conditions and exhibit very varying levels of antiviral activity against Zika virus.

Method B. Compound in Extract Form

An extract containing a target compound being tested is evaluated as detailed in Method A, except that the amount of extract is normalized to the amount of target compound in the extract. For example, an extract containing 2% wt of oleandrin contains 20 microg of oleandrin per 1 mg of extract. Accordingly, if the intended amount of oleandrin for evaluation is 20 microg, then 1 mg of extract would be used in the assay.

Example 7

Preparation of a Tablet Comprising Antiviral Composition

An initial tabletting mixture of 3% Syloid 244FP and 97% microcrystalline cellulose (MCC) was mixed. Then, an existing batch of composition prepared according to Example 3 was incorporated into the Syloid/MCC mixture via wet granulation. This mixture is labeled "Initial Tabletting Mixture) in the table below. Additional MCC was added extra-granularly to increase compressibility. This addition to the Initial Tabletting Mixture was labeled as "Extra-granular Addition." The resultant mixture from the extra-granular addition was the same composition as the "Final Tabletting Mixture."

| Component<br>Initial Tabletting Mixture | Weight (g) | Weight % (w/w) |
|---|---|---|
| Microcrystalline cellulose | 48.5 | 74.2 |
| Colloidal Silicon Dioxide/Syloid 244FP | 1.5 | 2.3 |
| Formulation from Ex. 3 | 15.351 | 23.5 |
| Total | 65.351 | 100.0 |

Extragranular Addition

| Component | Weight (g) | Weight % (w/w) |
|---|---|---|
| Initial Tabulating Mixture | 2.5 | 50.0 |
| Microcrystalline cellulose | 2.5 | 50.0 |
| Total | 5 | 100.0 |

Final Tabletting Mixture: Abbreviated

| Component | Weight (g) | Weight % (w/w) |
|---|---|---|
| Microcrystalline cellulose | 4.36 | 87.11 |
| Colloidal Silicon Dioxide/Syloid 244FP | 0.06 | 1.15 |
| Formulation from Ex. 3 | 0.59 | 11.75 |
| Total | 5.00 | 100 |

Final Tabletting Mixture: Detailed

| Component | Weight (g) | Weight % (w/w) |
|---|---|---|
| Microcrystalline cellulose | 4.36 | 87.11 |
| Colloidal Silicon Dioxide/Syloid 244FP | 0.06 | 1.15 |
| Vitamin E | 0.01 | 0.11 |
| Cremophor ELP | 0.33 | 6.56 |
| Labrasol | 0.05 | 1.01 |
| Glycerol Monooleate | 0.14 | 2.72 |
| Ethanol | 0.05 | 0.90 |
| SCF extract | 0.02 | 0.44 |
| Total | 5.00 | 100.00 |

Syloid 244FP is a colloidal silicon dioxide manufactured by Grace Davison. Colloidal silicon dioxide is commonly used to provide several functions, such as an adsorbant, glidant, and tablet disintegrant. Syloid 244FP was chosen for its ability to adsorb 3 times its weight in oil and for its 5.5 micron particle size.

Example 8

HPLC Analysis of Solutions Containing Oleandrin

Samples (oleandrin standard, SCF extract and hot-water extract) were analyzed on HPLC (Waters) using the following conditions: Symmetry C18 column (5.0 µm, 150×4.6 mm I.D.; Waters); Mobile phase of MeOH:water=54: 46 (v/v) and flow rate at 1.0 ml/min. Detection wavelength was set at 217 nm. The samples were prepared by dissolving the compound or extract in a fixed amount of HPLC solvent to achieve an approximate target concentration of oleandrin. The retention time of oleandrin can be determined by using an internal standard. The concentration of oleandrin can be determined/calibrated by developing a signal response curve using the internal standard.

Example 9

Preparation of Pharmaceutical Composition

A pharmaceutical composition of the invention can be prepared any of the following methods. Mixing can be done under wet or dry conditions. The pharmaceutical composition can be compacted, dried or both during preparation. The pharmaceutical composition can be portioned into dosage forms.

Method A.

At least one pharmaceutical excipient is mixed with at least one antiviral compound disclosed herein.

Method B.

At least one pharmaceutical excipient is mixed with at least two antiviral compounds disclosed herein.

Method C.

At least one pharmaceutical excipient is mixed with at least one cardiac glycosides disclosed herein.

Method D.

At least one pharmaceutical excipient is mixed with at least two triterpenes disclosed herein.

Method E.

At least one pharmaceutical excipient is mixed with at least one cardiac glycoside disclosed herein and at least two triterpenes disclosed herein.

Method D.

At least one pharmaceutical excipient is mixed with at least three triterpenes disclosed herein.

Example 10

Preparation of Triterpene Mixtures

The following compositions were made by mixing the specified triterpenes in the approximate molar ratios indicated.

| Composition | Triterpene (Approximate Relative Molar Content) | | |
|---|---|---|---|
| | Oleanolic acid (O) | Ursolic acid (U) | Betulinic acid (B) |
| I (A-C) | 3 | 2.2 | 1 |
| II (A-C) | 7.8 | 7.4 | 1 |
| III (A-C) | 10 | 1 | 1 |
| IV (A-C) | 1 | 10 | 1 |
| V (A-C) | 1 | 1 | 10 |
| VI (A-C) | 1 | 1 | 0 |
| VII (A-C) | 1 | 1 | 1 |
| VIII (A-C) | 10 | 1 | 0 |
| IX (A-C) | 1 | 10 | 0 |

For each composition, three different respective solutions were made, whereby the total concentration of triterpenes in each solution was approximately 9 µM, 18 µM, or 36 µM.

| Composition (total triterpene content, µM) | Triterpene (Approximate Content of Each, µM) | | |
|---|---|---|---|
| | Oleanolic acid (O) | Ursolic acid (U) | Betulinic acid (B) |
| I-A (36) | 17.4 | 12.8 | 5.8 |
| I-B (18) | 8.7 | 6.4 | 2.9 |
| I-C (9) | 4.4 | 3.2 | 1.5 |
| II-A (36) | 17.3 | 16.4 | 2.2 |
| II-B (18) | 8.7 | 8.2 | 1.1 |
| II-C (9) | 4.3 | 4.1 | 0.6 |
| III-A (36) | 30 | 3 | 3 |
| III-B (18) | 15 | 1.5 | 1.5 |
| III-C (9) | 7.5 | 0.75 | 0.75 |
| IV-A (36) | 3 | 30 | 3 |
| IV-B (18) | 1.5 | 15 | 1.5 |
| IV-C (9) | 0.75 | 7.5 | 0.75 |
| V-A (36) | 3 | 3 | 30 |
| V-B (18) | 1.5 | 1.5 | 15 |
| V-C (9) | 0.75 | 0.75 | 7.5 |
| VI-A (36) | 18 | 18 | 0 |
| VI-B (18) | 9 | 9 | 0 |
| VI-C (9) | 4.5 | 4.5 | 0 |
| VII-A (36) | 12 | 12 | 12 |
| VII-B (18) | 6 | 6 | 6 |
| VII-C (9) | 3 | 3 | 3 |
| VIII-A (36) | 32.7 | 3.3 | 0 |
| VIII-B (18) | 16.35 | 1.65 | 0 |
| VIII-C (9) | 8.2 | 0.8 | 0 |
| IX-A (36) | 3.3 | 32.7 | 0 |
| IX-B (18) | 1.65 | 16.35 | 0 |
| IX-C (9) | 0.8 | 8.2 | 0 |

Example 11

Preparation of Antiviral Compositions

Antiviral compositions can be prepared by mixing the individual triterpene components thereof to form a mixture. The triterpene mixtures prepared above that provided acceptable antiviral activity were formulated into antiviral compositions.

Antiviral Composition with Oleanolic Acid and Ursolic Acid

Known amounts of oleanolic acid and ursolic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable antiviral composition, at least one pharmaceutically acceptable excipient was mixed in with the pharmacologically active agents. An antiviral composition is formulated for administration to a mammal.

Antiviral Composition with Oleanolic Acid and Betulinic Acid

Known amounts of oleanolic acid and betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable antiviral composition, at least one pharmaceutically acceptable excipient was mixed in with the pharmacologically active agents. An antiviral composition is formulated for administration to a mammal.

Antiviral Composition with Oleanolic Acid, Ursolic Acid, and Betulinic Acid

Known amounts of oleanolic acid, ursolic acid and betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable antiviral composition, at least one pharmaceutically acceptable excipient was mixed in with the pharmacologically active agents. An antiviral composition is formulated for administration to a mammal.

Antiviral Composition with Oleadrin, Oleanolic Acid, Ursolic Acid, and Betulinic Acid Known amounts of oleandrin oleanolic acid, ursolic acid and betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contained the components in the relative molar ratios as described herein.

For a pharmaceutically acceptable antiviral composition, at least one pharmaceutically acceptable excipient was mixed in with the pharmacologically active agents. An antiviral composition is formulated for administration to a mammal.

Example 12

Treatment of Filovirus Infection in a Subject

Exemplary Filovirus infections include Ebolavirus and Marburgvirus.

Method A. Antiviral Composition Therapy

A subject presenting with Filovirus infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's Filovirus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.

Method B. Combination Therapy: Antiviral Composition with Another Agent

Method A, above, is followed except that the subject is prescribed and administered one or more other therapeutic agents for the treatment of Filovirus infection or symptoms thereof. Then one or more other therapeutic agents can be administered before, after or with the antiviral composition. Dose escalation (or de-escalation) of the one or more other therapeutic agents can also be done.

Example 13

Treatment of *Flavivirus* Infection in a Subject

Exemplary *Flavivirus* infections include Yellow Fever, Dengue Fever, Japanese Enchephalitis, West Nile Viruses, Zikavirus, Tick-borne Encephalitis, Kyasanur Forest Disease, Alkhurma Disease, Chikungunya virus, Omsk Hemorrhagic Fever, Powassan virus infection.

Method A. Antiviral Composition Therapy

A subject presenting with *Flavivirus* infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's *Flavivirus* titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.

Method B. Combination Therapy: Antiviral Composition with Another Agent

Method A, above, is followed except that the subject is prescribed and administered one or more other therapeutic agents for the treatment of *Flavivirus* infection or symptoms thereof. Then one or more other therapeutic agents can be administered before, after or with the antiviral composition. Dose escalation (or de-escalation) of the one or more other therapeutic agents can also be done.

Example 14

Evaluation of Antiviral Activity Against Zikavirus and Dengue Virus

A CPE-based antiviral assay was performed by infecting target cells in the presence or absence of test compositions, at a range of concentrations. Infection of target cells by results in cytopathic effects and cell death. In this type of assay, reduction of CPE in the presence of test composition, and the corresponding increase in cell viability, is used as an indicator of antiviral activity. For CPE-based assays, cell viability was determined with a neutral red readout. Viable cells incorporate neutral red in their lysosomes. Uptake of neutral red relies on the ability of live cells to maintain a lower pH inside their lysosomes than in the cytoplasm, and this active process requires ATP. Once inside the lysosome, the neutral red dye becomes charged and is retained intracellularly. After a 3-hour incubation with neutral red (0.033%), the extracellular dye was removed, cells were washed with PBS, and the intracellular neutral red was solubilized with a solution of 50% ethanol+1% acetic acid. The amount of neutral red in solution was quantified by reading the absorbance (optical density) of each well at 490 nm Adherent cell lines were used to evaluate the antiviral activity of compositions against a panel of viruses. Compositions were pre-incubated with the target cells for 30 min before the addition of virus to the cells. The compositions were present in the cell culture medium for the duration of the infection incubation period. For each infection assay, a viability assay was set up in parallel using the same concentrations of compositions (duplicates) to determine cytotoxicity effects of the compositions in the absence of virus.

The antiviral activity of test compositions was determined by comparing infection levels (for immunostaining-based assay) or viability (for CPE-based assays) of cells under test conditions to the infection level or viability of uninfected cells. Cytotoxic effects were evaluated in uninfected cells by comparing viability in the presence of inhibitors to the viability of mock-treated cells. Cytotoxicity was determined by an XTT viability assay, which was conducted at the same timepoint as the readout for the corresponding infection assay.

Test compositions were dissolved in 100% methanol. Eight concentrations of the compositions were generated (in duplicate) by performing 8-fold dilutions, starting with 50 μM as the highest concentration tested. The highest test concentration of composition (50 μM) resulted in a 0.25% final concentration of methanol (v/v %) in the culture medium. An 8-fold dilution series of methanol vehicle was included in each assay plate, with concentrations mirroring the final concentration of methanol in each composition test condition. When possible, the EC50 and CC50 of the composition was determined for each assay using GraphPad Prism software.

Antiviral activity was evaluated by the degree of protection against virus-induced cytopathic effects (CPE). Cells were challenged with virus in the presence of different concentrations of control or compositions. The extent of protection against CPE was monitored after 6 days (ZIKV, Zikavirus) or 7 days (DENV, Dengue virus) post infection by quantifying cell viability in different test conditions and comparing values with that of untreated cells and cells treated with vehicle alone (infection medium).

Quality controls for the neutralization assay were performed on every plate to determine: i) signal to background (S/B) values; ii) inhibition by the known inhibitors, and iii) variation of the assay, as measured by the coefficient of variation (C.V.) of all data points. Overall variation in the infection assays ranged from 3.4% to 9.5%, and overall variation in the viability assays ranged from 1.4% to 3.2%, calculated as the average of all C.V. values. The signal-to-background (S/B) for the infection assays ranged from 2.9 to 11.0, while the signal-to-background (S/B) for the viability assays ranged from 6.5 to 29.9.

Protection of DENV2-induced cytopathic effect (CPE) with Neutral Red readout: For the DENV2 antiviral assay, the 08-10381 Montserrat strain was used. Viral stocks were generated in C6/36 insect cells. Vero cells (epithelial kidney cells derived from *Cercopithecus aethiops*) were maintained in MEM with 5% FBS (MEMS). For both the infection and the viability assays, cells were seeded at 10,000 cells per well in 96-well clear flat bottom plates and maintained in MEMS at 37° C. for 24 hours. The day of infection, samples were diluted 8-fold in U-bottom plates using MEM with 1% bovine serum albumin (BSA). Test material dilutions were prepared at 1.25× the final concentration and 40 μl were incubated with the target cells at 37° C. for 30 minutes. Following the test material pre-incubation, 10 μl of virus dilutions prepared in MEM with 1% BSA was added to each well (50 μl final volume per well) and plates were incubated at 37° C. in a humidified incubator with 5% $CO_2$ for 3 hours. The volume of virus used in the assay was previously determined to produce a signal in the linear range inhibited by Ribavirin and compound A3, known inhibitors of DENV2. After the infection incubation, cells were washed with PBS, then MEM containing 2% FBS (MEM2) to remove unbound virus. Subsequently, 50 μl of medium containing inhibitor dilutions prepared at a 1× concentration in MEM2 was added to each well. The plate was incubated at 37° C. in the incubator (5% CO2) for 7 days. Controls with no virus ("mock-infected'), infected cells incubated with medium alone, infected cells incubated with vehicle alone (methanol), and wells without cells (to determine background) were included in the assay plate. Control wells containing 50 μM Ribavirin and 0.504 compound A3 were also included on the assay plate. After 7 days of infection, cells were stained with neutral red to monitor cell viability. Test materials were evaluated in duplicates using serial 8-fold dilutions in infection medium. Controls included cells incubated with no virus ("mock-infected"), infected cells incubated with medium alone, or infected cells in the presence of Ribavirin (0.5 μM) or A3 (0.5 μM). A full duplicate inhibition curve with methanol vehicle only was included on the same assay plate.

Protection of ZIKV-induced cytopathic effect (CPE) with Neutral Red readout: For the ZIKV antiviral assay, the PLCal_ZV strain was used. Vero cells (epithelial kidney cells derived from *Cercopithecus aethiops*) were maintained in MEM with 5% FBS (MEM5). For both the infection and the viability assays, cells were seeded at 10,000 cells per well in 96-well clear flat bottom plates and maintained in MEM5 at 37° C. for 24 hours. The day of infection, samples were diluted 8-fold in U-bottom plates using MEM with 1% bovine serum albumin (BSA). Test material dilutions were prepared at 1.25× the final concentration and 40 μl were incubated with the target cells at 37° C. for 30 minutes. Following the test material pre-incubation, 10 μl of virus dilutions prepared in MEM with 1% BSA was added to each well (50 μl final volume per well) and plates were incubated at 37° C. in a humidified incubator with 5% CO2 for 3 hours. After the infection incubation, cells were washed with PBS, then MEM containing 2% FBS (MEM2) to remove unbound virus. Subsequently, 50 μl of medium containing inhibitor dilutions prepared at a 1× concentration in MEM2 was added to each well. The plate was incubated at 37° C. in the incubator (5% CO2) for 6 days. Controls with no virus ("mock-infected'), infected cells incubated with medium alone, infected cells incubated with vehicle alone (methanol), and wells without cells (to determine background) were included in the assay plate. After 6 days of infection, cells were stained with neutral red to monitor cell viability. Test materials were evaluated in duplicates using serial 8-fold dilutions in infection medium. Controls included cells incubated with no virus ("mock-infected"), infected cells incubated with medium alone, or infected cells in the presence of A3 (0.5 μM). A full duplicate inhibition curve with methanol vehicle only was included on the same assay plate.

Analysis of CPE-based viability data: for the neutral red assays, cell viability was determined by monitoring the absorbance at 490 nm. The average signal obtained in wells with no cells was subtracted from all samples. Then, all data points were calculated as a percentage of the average signal observed in the 8 wells of mock (uninfected) cells on the same assay plate. Infected cells treated with medium alone reduced the signal to an average of 4.2% (for HRV), 26.9% (for DENV), and 5.1% (for ZIKV) of that observed in uninfected cells. The signal-to-background (S/B) for this assay was 2.9 (for DENV), and 7.2 (for ZIKV), determined as the viability percentage in "mock-infected" cells compared to that of infected cells treated with vehicle only.

Viability assay (XTT) to assess compound-induced cytotoxicity: Mock-infected cells were incubated with inhibitor dilutions (or medium only) using the same experimental setup and inhibitor concentrations as was used in the corresponding infection assay. The incubation temperature and duration of the incubation period mirrored the conditions of the corresponding infection assay. Cell viability was evaluated with an XTT method. The XTT assay measures mitochondrial activity and is based on the cleavage of yellow tetrazolium salt (XTT), which forms an orange formazan dye. The reaction only occurs in viable cells with active mitochondria. The formazan dye is directly quantified using a scanning multi-well spectrophotometer. Background levels obtained from wells with no cells were subtracted from all data-points. Controls with methanol vehicle alone (at 7 concentrations mirroring the final percent methanol of each Oleandrin test wells) were included in the viability assay plate. The extent of viability was monitored by measuring absorbance at 490 nm.

Analysis of cytotoxicity data: For the XTT assays, cell viability was determined by monitoring the absorbance at 490 nm. The average signal obtained in wells with no cells was subtracted from all samples. Then, all data points were calculated as a percentage of the average signal observed in the 8 wells of mock (uninfected) cells on the same assay plate. The signal-to-background (S/B) for this assay was 29.9 (for IVA), 8.7 (for HRV), 6.5 (for DENV), and 6.7 (for ZIKV), determined as the viability percentage in "mock-infected" cells compared to the signal observed for wells without cells.

Example 15

Evaluation of Antiviral Activity Against Filovirus (Ebolavirus and Marburgvirus)

Method A.

Vero E6 cells were infected with EBOV/Kik (A, MOI=1) or MARV/Ci67 (B, MOI=1) in the presence of oleandrin, digoxin or PBI-05204, an oleandrin-containing plant extract. After 1 hr, inoculum and compounds were removed and fresh medium added to cells. 48 hr later, cells were fixed and immunostained to detect cells infected with EBOV or MARV. Infected cells were enumerated using an Operetta. C) Vero E6 were treated with compound as above. ATP levels were measured by CellTiter-Glo as a measurement of cell viability.
Method B.
Vero E6 cells were infected with EBOV (A,B) or MARV (C,D). At 2 hr post-infection (A,C) or 24 hr post-infection (B,D), oleandrin or PBI-05204 was added to cells for 1 hr, then discarded and cells were returned to culture medium. At 48 hr post-infection, infected cells were analyzed as in FIG. 1.
Method C.
Vero E6 cells were infected with EBOV or MARV in the presence of oleandrin or PBI-05204 and incubated for 48 hr. Supernatants from infected cell cultures were passaged onto fresh Vero E6 cells, incubated for 1 hr, then discarded (as depicted in A). Cells containing passaged supernatant were incubated for 48 hr. Cells infected with EBOV (B) or MARV (C) were detected as described previously. Control infection rates were 66% for EBOV and 67% for MARV.

Example 16

Evaluation of Antiviral Activity Against Togaviridae Virus

Alphavirus: VEEV and WEEV

Vero E6 cells were infected with Venezuelan equine encephalitis virus (A, MOI=0.01) or Western equine encephalitis virus (B, MOI=0.1) for 18 hr in the presence or absence of indicated compounds. Infected cells were detected as described herein and enumerated on an Operetta.

Example 17

Treatment of Paramyxoviridae Infection in a Subject

Exemplary Paramyxoviridae family viral infections include Henipavirus genus infection, Nipah virus infection, or Hendra virus infection.
Method A. Antiviral Composition Therapy
A subject presenting with Paramyxoviridae family infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's virus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.
Method B. Combination Therapy: Antiviral Composition with Another Agent
Method A, above, is followed except that the subject is prescribed and administered one or more other therapeutic agents for the treatment of Paramyxoviridae family infection or symptoms thereof. Then one or more other therapeutic agents can be administered before, after or with the antiviral composition. Dose escalation (or de-escalation) of the one or more other therapeutic agents can also be done.

Example 18

Cell-lines and Isolation of Primary huPBMC's

The virus-producing HTLV-1-transformed (HTLV-1+) SLB1 lymphoma T-cell-line (Arnold et al., 2008; kindly provided by P. Green, The Ohio State University-Comprehensive Cancer Center) was cultured in a humidified incubator at 37° C. under 10% $CO_2$ in Iscove's Modified Dulbecco's Medium (IMDM; ATCC No. 30-2005), supplemented with 10% heat-inactivated fetal bovine serum (FBS; Biowest), 100 U/ml penicillin, 100 µg/ml streptomycin-sulfate, and 20 µg/ml gentamycin-sulfate (Life Technologies).
Primary human peripheral blood mononuclear cells (huPBMCs) were isolated from whole blood samples, provided without identifiers by the SMU Memorial Health Center under a protocol approved by the SMU Institutional Review Board and consistent with Declaration of Helsinki principles. In brief, 2 ml of whole blood was mixed with an equal volume of sterile phosphate-buffered saline (PBS), pH 7.4, in polypropylene conical tubes (Corning) and then the samples were gently layered over 3 ml of Lymphocyte Separation Medium (MP Biomedicals). The samples were centrifuged for 30 min at 400×g in a swinging bucket rotor at room temp. The buffy-coat huPBMCs were subsequently aspirated, washed 2× in RPMI-1640 medium (ATCC No. 30-2001), and pelleted by centrifugation for 7 min at 260×g. The cells were resuspended in RPMI-1640 medium, supplemented with 20% FBS, 100 U/ml penicillin, 100 µg/ml streptomycin-sulfate, 20 µg/ml gentamycin-sulfate, and 50 U/ml recombinant human interleukin-2 (hu-IL-2; Roche Applied Science), and stimulated for 24 hrs with 10 ng/ml phytohemagglutinin (PHA; Sigma-Aldrich) and grown at 37° C. under 10% $CO_2$ in a humidified incubator. On the following day, the cells were pelleted by centrifugation for 7 min at 260×g and washed 2× with RPMI-1640 medium to remove the PHA, and then resuspended and cultured in complete medium, supplemented with antibiotics and 50 U/ml hu-IL-2.

Example 19

Generation of GFP-Expressing HTLV-1+ SLB1/pLenti-GFP T-Cell Clones

To generate the GFP-expressing HTLV-1+ SLB1 T-cell clones, 2×10$^6$ SLB1 cells were plated in 60 mm$^2$ tissue-culture dishes (Corning) in IMDM, supplemented with 10% heat-inactivated FBS and antibiotics, and then transduced with lentiviral particles containing a pLenti-6.2/V5-DEST-green fluorescent protein expression vector which also carries a blasticidin-resistance gene. After 6 hrs, the transduced cells were pelleted by centrifugation for 7 min at 260×g at room temperature, washed 2× with serum-free IMDM, and resuspended in complete medium supplemented with 5 µg/ml blasticidin (Life Technologies) and aliquoted into 96-well microtiter plates (Corning). The cultures were maintained with blasticidin-selection for two weeks in a humidified incubator at 37° C. and 10% $CO_2$. The GFP-expressing lymphoblasts were screened by fluorescence-microscopy, and then plated by limiting-dilution in 96-well microtiter plates to obtain homogenous GFP-expressing cell clones.

The resulting HTLV-1+ SLB1/pLenti-GFP T-lymphocyte clones were expanded and repeatedly passaged; and the expression of GFP was confirmed by sodium dodecyl sulfate-polyacrylamide gel electrophoresis (SDS-PAGE) and immunoblotting using a rabbit polyclonal Anti-GFP (FL) antibody (Santa Cruz Biotechnology).

Example 20

Quantitation of Virus Production and Particle Infectivity by Anti-HTLV-1 p19$^{Gag}$ ELISA's To determine the effects of oleandrin or an extract of N. oleander upon HTLV-1 proviral replication and the release of newly-synthesized extracellular virus particles, the HTLV-1+ SLB1 lymphoma T-cell-line was plated at 2×10$^4$ cells per well in 300 μl of complete medium, supplemented with antibiotics, in 96-well microtiter plates and incubated at 37° C. under 10% $CO_2$. The purified oleandrin compound and extract of N. oleander (Phoenix Biotechnology; see Singh et al., 2013) were resuspended in the Vehicle solution (20% v/v dimethyl sulfoxide, DMSO, in MilliQ distilled/deionized $H_2O$) at a stock concentration of 2 mg/ml and then sterilized using a luer-lock 0.2 μm syringe filter (Millipore). The HTLV-1+ SLB1 cells were treated with oleandrin or the N. oleander extract at concentrations of 10, 50, and 100 μg/ml, or with increasing amounts (1.5, 7.5, and 150 of the Vehicle control for 72 hrs. The 96-well microtiter plates were then centrifuged for 7 min at 260×g at room temp using an Eppendorf A-2-DWP swinging plate rotor to pellet the cells, and the levels of extracellular p19$^{Gag}$-containing HTLV-1 particles released into the culture supernatants were quantified relative to a p19$^{Gag}$ protein standard by performing colorimetric Anti-p19$^{Gag}$ enzyme-linked immunosorbent assays (ELISAs; Zeptometrix). The samples were analyzed with triplicate replicates on a Berthold Tristar LB 941 multimode microplate-reader at 450 nm in absorbance mode.

To assess the infectivity of newly-synthesized extracellular HTLV-1 particles collected from oleandrin-treated cells, 2×10$^4$ HTLV-1+ SLB1 T-lymphoblasts were plated in 300 μl of complete medium, supplemented with antibiotics, and the cultures were treated for 72 hrs with increasing concentrations (10, 50, and 100 μg/ml) of oleandrin or a N. oleander extract, or the Vehicle control (1.5, 7.5, and 15 μl). Then, 50 μl of the virus-containing supernatants were used to directly infect huPBMCs plated at a density of 2×10$^4$ cells per well on 96-well microtiter plates in complete medium, supplemented with antibiotics and hu-IL-2. The oleandrin compound, N. oleander extract, or Vehicle control were maintained in the huPBMCs culture medium to control for possible re-infection events by newly-produced particles. After 72 hrs, the relative levels of extracellular p19$^{Gag}$-containing HTLV-1 virions released into the culture supernatants by the infected huPBMCs were quantified through Anti-HTLV-1 p19$^{Gag}$ ELISAs.

Example 21

Measuring Cellular Apoptosis

To assess the relative cytotoxicity of the oleandrin compound, extract of N. oleander, or the Vehicle control in treated cell cultures, 2×10$^4$ HTLV-1+ SLB1 lymphoma T-cells or activated/cultured huPBMCs were plated in 300 μl of complete medium, supplemented with antibiotics, and maintained at 37° C. under 10% $CO_2$ in a humidified incubator. The cultures were treated with either increasing concentrations (10, 50, and 100 μg/ml) of oleandrin or N. oleander extract, or the Vehicle control (1.5, 7.5, 15 ml) and incubated for 72 hrs. Cyclophosphamide (50 μM; Sigma-Aldrich)-treated cells were included as a positive control for apoptosis. The cells were then aspirated and plated on Permanox 8-chamber tissue-culture slides (Nalge) that had been pre-treated with a sterile 0.01% solution of Poly-L-Lysine and Concanavalin A (1 mg/ml; Sigma-Aldrich). The samples were subsequently stained using a microscopy apoptosis detection kit with Annexin V conjugated to fluorescein isothiocyanate (Annexin V-FITC) and propidium iodide (PI; BD-Pharmingen), and the relative percentages of apoptotic (i.e., Annexin V-FITC and/or PI- positive) cells per field were quantified in-triplicate by confocal fluorescence-microscopy using a 20× objective lens. The total numbers of cells per field were quantified by microscopy using a DIC phase-contrast filter.

Example 22

HTLV-1 Transmission and Virological Synapse Formation in Co-Culture Assays

As the transmission of HTLV-1 typically occurs through direct contact between an infected cell and uninfected target cell across a virological synapse (Igakura et al., 2003; Pais-Correia et al., 2010; Gross et al., 2016; Omsland et al., 2018; Majorovits et al., 2008), we tested whether oleandrin, a N. oleander extract, or the Vehicle control might influence the formation of virological synapses and/or the transmission of infectious HTLV-1 particles via intercellular interactions in vitro. For these experiments, 2×10$^4$ virus-producing HTLV-1+ SLB1 T-cells were plated in 96-well microtiter plates and treated with mitomycin C (100 μg/ml) in 300 μl of complete medium for 2 hrs at 37° C. under 10% $CO_2$ (Bryja et al., 2006). The culture media was then removed, the cells were washed 2× with serum-free IMDM, and the cells were treated for either 15 min or 3 hrs with increasing amounts (10, 50, and 100 μg/ml) of oleandrin or N. oleander extract, or the Vehicle control (1.5, 7.5, and 15 μl). Alternatively, 2×10$^4$ of the GFP-expressing HTLV-1+ SLB1/pLenti-GFP T-cells were plated on 8-chamber tissue-culture slides in 300 μl of complete medium and treated with mitomycin C, washed 2× with serum-free IMDM, and then treated with oleandrin, N. oleander extract, or the Vehicle control as described for confocal microscopy experiments. We next aspirated the medium, washed the HTLV-1+ SLB1 cells 2× with serum-free medium, and added 2×10$^4$ huPBMCs to each well in 300 μl of RPMI-1640 medium, supplemented with 20% FBS, antibiotics and 50 U/ml hu-IL-2, and then co-cultured the cells for another 72 hrs (the cells were co-cultured for 6 hrs to visualize virological synapse formation and viral transmission by confocal microscopy using the SLB1/pLenti-GFP lymphoblasts) at 37° C. under 10% $CO_2$ in a humidified incubator. As a negative control, huPBMCs were cultured alone in the absence of virus-producing cells. The oleandrin, N. oleander extract, and Vehicle were maintained in the co-culture medium. The relative levels of extracellular p19$^{Gag}$-containing HTLV-1 particles released into the co-culture supernatants as a result of intercellular viral transmission were quantified by performing Anti-HTLV-1 p19$^{Gag}$ ELISAs. Virological synapses formed between the GFP-positive HTLV-1+ SLB/pLenti-GFP cells and huPBMCs were visualized using immunofluorescence-confocal microscopy by staining the fixed samples with an Anti-HTLV-1 gp21$^{Env}$ primary antibody and a rhodamine red-conjugated secondary antibody. Diamidino-2-phenyl-indole, dihydrochloride (DAPI; Molecular Probes) nuclear-staining was included for comparison and to visualize uninfected (i.e., HTLV-1-negative) cells. The intercellular transmission of HTLV-1 to the huPBMCs in co-culture assays was quantified by counting the relative percentages of HTLV-1 gp21$^{Env}$-positive (and GFP-negative) huPBMCs in 20 visual fields using a 20× objective lens.

Example 23

Microscopy

The Annexin V-FITC/PI-stained samples to quantify cellular apoptosis and cytotoxicity were visualized by confocal fluorescence-microscopy on a Zeiss LSM800 instrument equipped with an Airyscan detector and stage $CO_2$ incubator, using a Plan-Apochromat 20×/0.8 objective lens and Zeiss ZEN system software (Carl Zeiss Microscopy). The formation of virological synapses and viral transmission (i.e., determined by quantifying the relative percentages of Anti-HTLV-1 gp21$^{Env}$-positive huPBMCs) between the mitomycin C-treated HTLV-1+ SLB1/pLenti-GFP lymphoblasts and cultured huPBMCs were visualized by immunofluorescence-confocal microscopy using a Plan-Apochromat 20×/0.8 objective lens. The relative fluorescence-intensities of the DAPI, Anti-HTLV-1 gp21$^{Env}$-specific (rhodamine red-positive), and GFP signals were graphically quantified using the Zen 2.5D analysis tool (Carl Zeiss Microscopy). The GFP-expressing HTLV-1+ SLB1/pLenti-GFP T-cell clones were screened by confocal fluorescence-microscopy on a Nikon Eclipse TE2000-U inverted microscope and D-Eclipse confocal imaging system, equipped with 633 nm and 543 nm He/Ne and 488 nm Ar lasers, using a Plan Fluor 10×/0.30 objective lens and DIC phase-contrast filter (Nikon Instruments).

Example 24

Statistical Analysis

The statistical significance of experimental data sets was determined using unpaired two-tailed Student's t-tests (alpha=0.05) and calculated P-values using the Shapiro-Wilk normality test and Graphpad Prism 7.03 software. The P-values were defined as: 0.1234 (ns), 0.0332 (*), 0.0021 (), 0.0002 (*), <0.0001 (****). Unless otherwise noted, error bars represent the SEM from at least three independent experiments.

Example 25

Treatment of *Deltaretrovirus* Infection in a Subject

Exemplary *Deltaretrovirus* infections include HTLV-1.
Method A. Antiviral Composition Therapy A subject presenting with HTLV-1 infection is prescribed antiviral composition, and therapeutically relevant doses are administered to the subject according to a prescribed dosing regimen for a period of time. The subject's level of therapeutic response is determined periodically. The level of therapeutic response can be determined by determining the subject's HTLV-1 virus titre in blood or plasma. If the level of therapeutic response is too low at one dose, then the dose is escalated according to a predetermined dose escalation schedule until the desired level of therapeutic response in the subject is achieved. Treatment of the subject with antiviral composition is continued as needed and the dose or dosing regimen can be adjusted as needed until the patient reaches the desired clinical endpoint.
Method B. Combination Therapy: Antiviral Composition with Another Agent Method A, above, is followed except that the subject is prescribed and administered one or more other therapeutic agents for the treatment of HTLV-1 infection or symptoms thereof. Then one or more other therapeutic agents can be administered before, after or with the antiviral composition. Dose escalation (or de-escalation) of the one or more other therapeutic agents can also be done. Exemplary other therapeutic agents are described herein.

As used herein, the term "about" or "approximately" are taken to mean ±10%, ±5%, ±2.5% or ±1% of a specified valued. As used herein, the term "substantially" is taken to mean "to a large degree" or "at least a majority of" or "more than 50% of"

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating a viral infection, caused by Filovirus, Ebolavirus or Marburgvirus, in a subject in need thereof, the method comprising administering to the subject one or more therapeutically effective doses of an antiviral composition comprising digoxin, wherein following administration of said one or more doses, the plasma concentration of digoxin in said subject is in the range of about 0.05 to about 2.5 ng/mL, in terms of the amount of digoxin per mL of plasma, and wherein said antiviral composition is administered immediately after infection or any time within one day to 5 days after infection or at the earliest time after definite diagnosis of infection with virus.

2. A prophylactic method of treating a subject at risk of contracting a viral infection, caused by Filovirus, Ebolavirus or Marburgvirus, the method comprising chronically administering to the subject one or more therapeutically effective doses of an antiviral composition on a recurring basis over an extended treatment period prior to the subject contracting the viral infection, thereby preventing the subject from contracting the viral infection; wherein the antiviral composition comprises digoxin, and wherein following administration of said one or more doses, the plasma concentration of digoxin in said subject is in the range of about 0.05 to about 2.5 ng/mL, in terms of the amount of digoxin per mL of plasma.

3. The method of claim 1 comprising:
determining whether or not the subject has said viral infection;
indicating administration of said antiviral composition;
administering an initial dose of said antiviral composition to the subject according to a prescribed initial dosing regimen for a period of time;
periodically determining the adequacy of subject's clinical response and/or therapeutic response to treatment with said antiviral composition; and
if the subject's clinical response and/or therapeutic response is adequate, then continuing treatment with said antiviral composition as needed until the desired clinical endpoint is achieved; or if the subject's clinical response and/or therapeutic response are inadequate at the initial dose and initial dosing regimen, then escalating or deescalating the dose until the desired clinical response and/or therapeutic response in the subject is achieved.

4. The method of claim 1, wherein the viral titer in the subject's blood or plasma is reduced or does not increase as a result of the treatment.

5. The method of claim 1, wherein one or more doses are administered on a daily, weekly or monthly basis.

6. The method of claim 1, wherein the administration is systemic, parenteral, buccal, enteral, intramuscular, subdermal, sublingual, peroral, oral, or a combination thereof.

7. The method of claim 1, wherein the amount of digoxin administered per day is selected from the group consisting of 140 microg to 315 microg, 20 microg to 750 microg, 12 microg to 300 microg, 12 microg to 120 microg, 0.01 microg to 100 microg, about 0.5 to about 100 microg, about 1 to about 80 microg, about 1.5 to about 60 microg, about 1.8 to about 60 microg, or about 1.8 to about 40 microg.

8. The method of claim 1, wherein a dose of said antiviral composition is administered twice daily or about every 12 hours, and the amount of digoxin in said dose is about 0.25 to about 50 microg or about 0.9 to 5 microg.

9. The method of claim 1, wherein said antiviral composition is administered as primary antiviral therapy, adjunct antiviral therapy, or co-antiviral therapy.

10. The method of claim 1, wherein said administration comprises separate administration or coadministration of said antiviral composition with at least one other antiviral composition or with at least one other composition for treating symptoms associated with said viral infection.

11. The method according to claim 10, wherein said symptoms are selected from the group consisting of inflammation, vomiting, nausea, headache, fever, diarrhea, nausea, hives, conjunctivitis, malaise, muscle pain, joint pain, seizure, and paralysis.

\* \* \* \* \*